(12) United States Patent
Yoon et al.

(10) Patent No.: US 11,844,818 B2
(45) Date of Patent: Dec. 19, 2023

(54) AEROMONAS HYDROPHILA BACTERIOPHAGE AER-HYP-3 AND USE THEREOF FOR INHIBITING GROWTH OF AEROMONAS HYDROPHILA BACTERIA

(71) Applicant: Intron Biotechnology, Inc., Gyeonggi-do (KR)

(72) Inventors: Seong Jun Yoon, Seoul (KR); Soo Youn Jun, Seoul (KR); An Sung Kwon, Gyeonggi-do (KR); Ji In Jung, Seoul (KR); Sang Hyeon Kang, Seoul (KR)

(73) Assignee: Intron Biotechnology, Inc., Gyeonggi-do (KR)

( * ) Notice: Subject to any disclaimer, the term of this patent is extended or adjusted under 35 U.S.C. 154(b) by 646 days.

(21) Appl. No.: 16/970,052

(22) PCT Filed: Feb. 18, 2019

(86) PCT No.: PCT/KR2019/001901
§ 371 (c)(1),
(2) Date: Aug. 14, 2020

(87) PCT Pub. No.: WO2019/164195
PCT Pub. Date: Aug. 29, 2019

(65) Prior Publication Data
US 2021/0085733 A1   Mar. 25, 2021

(30) Foreign Application Priority Data

Feb. 23, 2018 (KR) .................. 10-2018-0021756

(51) Int. Cl.
*A61K 35/76* (2015.01)
*C12N 7/00* (2006.01)

(52) U.S. Cl.
CPC ............... *A61K 35/76* (2013.01); *C12N 7/00* (2013.01); *C12N 2795/10132* (2013.01)

(58) Field of Classification Search
CPC ............... A61K 35/76; C12N 7/00; C12N 2795/10132; C12N 2795/10121; A61P 31/04
See application file for complete search history.

(56) References Cited

U.S. PATENT DOCUMENTS

2013/0323209 A1   12/2013   Sung et al.

FOREIGN PATENT DOCUMENTS

| KR | 10-2014-0000107 | 1/2014 |
| KR | 10-1723827 | 4/2017 |
| WO | WO 2017/073916 | 5/2017 |

OTHER PUBLICATIONS

International Search Report and Written Opinion dated Jun. 10, 2019 by the International Searching Authority for International Application No. PCT/KR2019/001901, filed on Feb. 18, 2019 and published as WO 2019/164195 on Aug. 29, 2019 (Applicant—Intron Biotechnology, Inc.) (8 Pages).
Jun, J.W. et al., "Protective effects of the *Aeromonas* phages pAh1-C and pAh6-C against mass mortality of the cyprinid loach (*Misgurnuis anguillicaudatus*) caused by *Aeromonas hydrophila*," Aquaculture, 2013, vols. 416-417, pp. 289-295.
Park, S.H., "Isolation and characterization of Bacteriophage Specific for Aeromonas hydrophilia," Master's Thesis, School of Food Science & Biotechnology, Major in Food Biotechnology, The Graduate School Kyungpook National University, 2016, inner pp. 1-37.
Easwaran, M. et al. "Characterization of bacteriophage pAh-1 and its protective effects on experimental infection of Aeromonas hydrophilia in Zebrafish (*Danio rerio*)," Journal of Fish Diseases, Jun. 2017, vol. 40, No. 6, pp. 841-846.

*Primary Examiner* — Janet L Andres
*Assistant Examiner* — Ruixue Wang
(74) *Attorney, Agent, or Firm* — BALLARD SPAHR LLP

(57) ABSTRACT

The present invention relates to a Myoviridae bacteriophage Aer-HYP-3 (Accession number: KCTC 13479BP) isolated from nature, which has the ability to kill *Aeromonas hydrophila* bacteria and has the genome represented by SEQ ID NO: 1, and to a method of preventing and treating a disease caused by *Aeromonas hydrophila* bacteria using a composition containing the same as an active ingredient.

4 Claims, 2 Drawing Sheets

Specification includes a Sequence Listing.

[FIG. 1]
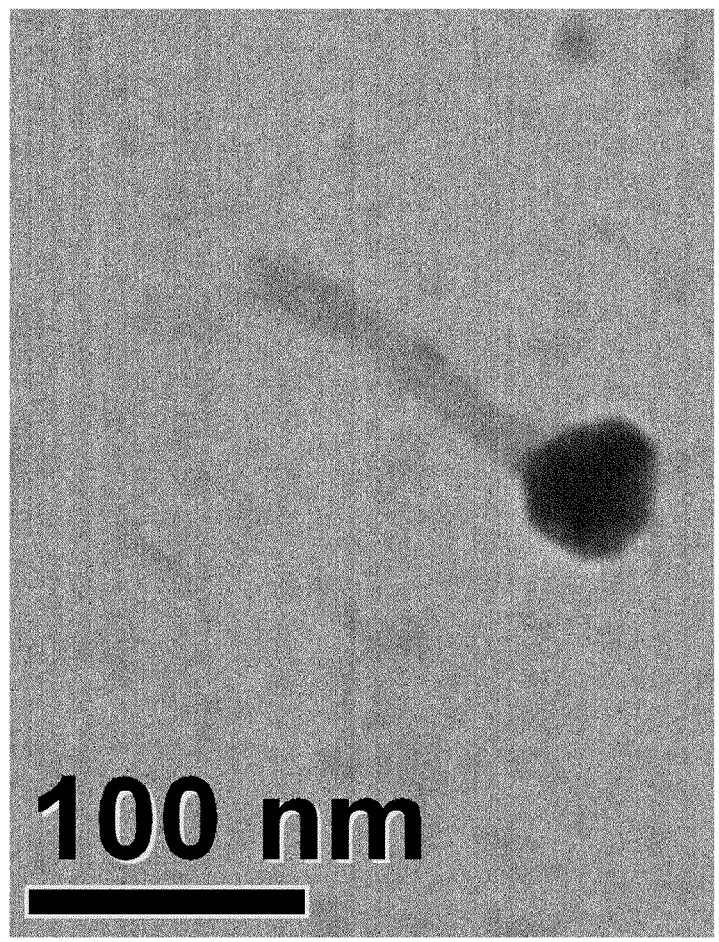

[FIG. 2]
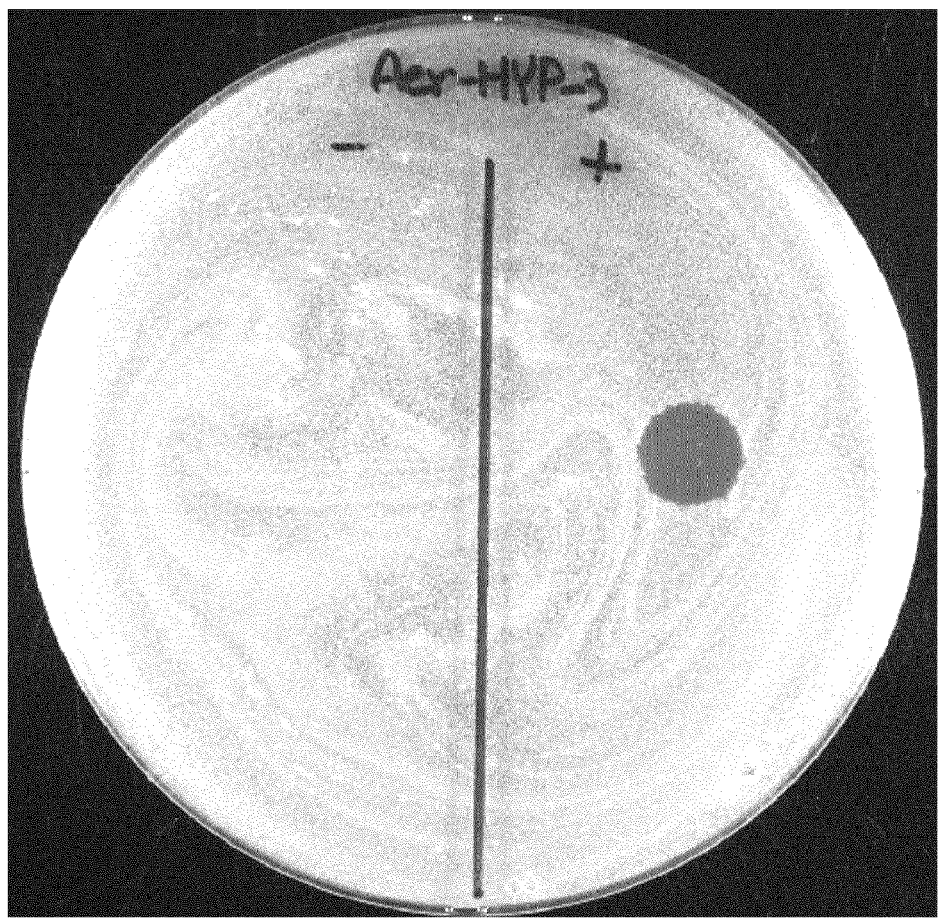

AEROMONAS HYDROPHILA BACTERIOPHAGE AER-HYP-3 AND USE THEREOF FOR INHIBITING GROWTH OF AEROMONAS HYDROPHILA BACTERIA

CROSS-REFERENCE TO RELATED APPLICATIONS

This application is a U.S. National Phase Application of International Application No. PCT/KR2019/001901, filed Feb. 18, 2019, which claims priority to Korean Application No. 10-2018-0021756, filed Feb. 23, 2018, each of which are hereby incorporated by reference in their entirety.

REFERENCE TO SEQUENCE LISTING

The Sequence Listing submitted concurrently with this preliminary amendment as a text file named "08162_0065U1_Sequence Listing.txt," created on Aug. 10, 2020, and having a size of 69,562 bytes is hereby incorporated by reference pursuant to 37 C.F.R. § 1.52(e)(5).

TECHNICAL FIELD

The present invention relates to a bacteriophage isolated from nature, which infects *Aeromonas hydrophila* bacteria to thus kill *Aeromonas hydrophila* bacteria, and a method of preventing and treating a disease caused by *Aeromonas hydrophila* bacteria using a composition containing the above bacteriophage as an active ingredient. More specifically, the present invention relates to a Myoviridae bacteriophage Aer-HYP-3 (Accession number: KCTC 13479BP) isolated from nature, which has the ability to kill *Aeromonas hydrophila* bacteria and has the genome represented by SEQ ID NO: 1, and a method of preventing and treating a disease caused by *Aeromonas hydrophila* bacteria using a composition containing the above bacteriophage as an active ingredient.

BACKGROUND ART

The *Aeromonas* genus, belonging to the gamma-proteobacteria, is a bacterium widely distributed around the world and is commonly found in soil and water, and some of these bacteria are opportunistic pathogens that may cause disease in humans. These bacteria are largely divided into non-motile *Aeromonas* genera and motile *Aeromonas* genera. *Aeromonas hydrophila* is a representative motile *Aeromonas* genus and is known to cause acute, chronic and latent infections through oral or transdermal infections to freshwater fish, amphibians, reptiles and humans. The serotypes of *Aeromonas hydrophila* are known to include thermo-stable somatic O antigen, thermo-labile capsular K antigen, and flagella H antigen, and most pathogenic *Aeromonas hydrophila* bacteria known to date are known to exhibit the thermo-stable somatic O antigen.

*Aeromonas hydrophila* causes systemic acute hemorrhagic septicemia in portions of fish that are affected and finally infected by stress due to various environmental factors such as temperature, intensive farming and organic matter in water and by wounds, parasite infections and other pathogens. In particular, in the case of infection with *Aeromonas hydrophila* bacteria at a high temperature, young salmon show large-scale mortality, black bass show red spot disease, and goldfish show secondary skin infection and furunculosis. Moreover, it is known that in warm-water fish farming, severe economic loss is caused by high mortality due to the *Aeromonas hydrophila* infection. Therefore, there is urgent need to develop methods that are applicable for preventing and further treating the *Aeromonas hydrophila* infection.

Although various antibiotics have been used for the prevention or treatment of diseases caused by *Aeromonas hydrophila*, the incidence of bacteria resistant to such antibiotics is increasing these days, and thus the development of other methods besides antibiotics is urgently required.

Recently, the use of bacteriophages as a countermeasure against infectious bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by the very high specificity thereof, and thus the range of types of bacteriophages that infect a specific bacterium is limited. That is, a certain bacteriophage may infect only a specific bacterium, suggesting that a certain bacteriophage is capable of providing an antibacterial effect only for a specific bacterium. Due to this bacterial specificity of bacteriophages, the bacteriophage confers antibacterial effects only upon a target bacterium, but does not affect commensal bacteria in the environment or in the interiors of animals. Conventional antibiotics, which have been widely used for bacterial treatment, incidentally influence many other kinds of bacteria. This causes problems such as environmental pollution and the disturbance of normal microflora in animals. In contrast, the use of bacteriophages does not disturb normal microflora in animals, because the target bacterium is selectively killed by use of bacteriophages. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in a filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As described above, bacteriophages tend to be highly specific for target bacteria. Because of the high specificity of bacteriophages to bacteria, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Aeromonas hydrophila*, many kinds of bacteriophages that exhibit antibacterial effects against *Aeromonas hydrophila* must be acquired. Furthermore, the resulting bacteriophages need to be screened as to whether or not they are superior to others in view of the aspects of antibacterial strength and spectrum.

DISCLOSURE

Technical Problem

Therefore, the present inventors endeavored to develop a composition applicable for the prevention or treatment of a disease caused by *Aeromonas hydrophila* using a bacteriophage that is isolated from nature and is capable of killing *Aeromonas hydrophila*, and further to establish a method of preventing and treating a disease caused by *Aeromonas hydrophila* using the composition. As a result, the present inventors isolated a bacteriophage suitable for this purpose from nature and determined the sequence of the genome, which distinguishes the isolated bacteriophage from other bacteriophages. Then, the present inventors developed a composition containing the bacteriophage as an active ingredient and ascertained that this composition is capable of being effectively used to prevent and treat a disease caused by *Aeromonas hydrophila*, thus culminating in the present invention.

Accordingly, an objective of the present invention is to provide a Myoviridae bacteriophage Aer-HYP-3 (Accession number: KCTC 13479BP) isolated from nature, which has the ability to specifically kill *Aeromonas hydrophila* and has the genome represented by SEQ ID NO: 1.

Another objective of the present invention is to provide a composition applicable for preventing and treating a disease caused by *Aeromonas hydrophila*, which contains, as an active ingredient, an isolated bacteriophage Aer-HYP-3 (Accession number: KCTC 13479BP), infecting *Aeromonas hydrophila*, to thus kill *Aeromonas hydrophila*.

Still another objective of the present invention is to provide a method of preventing and treating a disease caused by *Aeromonas hydrophila* using the composition applicable for preventing and treating a disease caused by *Aeromonas hydrophila*, which contains, as an active ingredient, the isolated bacteriophage Aer-HYP-3 (Accession number: KCTC 13479BP), infecting *Aeromonas hydrophila*, to thus kill *Aeromonas hydrophila*.

Yet another objective of the present invention is to provide a medicine bath agent (immersion agent) for preventing and treating a disease caused by *Aeromonas hydrophila* using the composition described above.

Still yet another objective of the present invention is to provide a feed additive effective upon farming by preventing and treating a disease caused by *Aeromonas hydrophila* using the composition described above.

Technical Solution

The present invention provides a Myoviridae bacteriophage Aer-HYP-3 (Accession number: KCTC 13479BP) isolated from nature, which has the ability to specifically kill *Aeromonas hydrophila* and has the genome represented by SEQ ID NO: 1, and a method of preventing and treating a disease caused by *Aeromonas hydrophila* using a composition containing the same as an active ingredient.

The bacteriophage Aer-HYP-3 was isolated by the present inventors and then deposited under the Budapest Treaty on the International Procedure at Korean Collection for Type Cultures, Korea Research Institute of Bioscience and Biotechnology (KRIBB), 125 Gwahak-ro, Yuseong-gu, Daijeon 305-806, Republic of Korea; the deposit was made on Feb. 7, 2018 (Accession number: KCTC 13479BP).

The present invention also provides a medicine bath agent and a feed additive applicable for the prevention and treatment of a disease caused by *Aeromonas hydrophila*, which contain the bacteriophage Aer-HYP-3 as an active ingredient.

Since the bacteriophage Aer-HYP-3 contained in the composition of the present invention kills *Aeromonas hydrophila* effectively, it is effective in the prevention (prevention of infection) and treatment (treatment of infection) of a disease caused by *Aeromonas hydrophila*. Therefore, the composition of the present invention is capable of being utilized for the prevention and treatment of a disease caused by *Aeromonas hydrophila*.

As used herein, the terms "prevention" and "prevent" refer to (i) prevention of an *Aeromonas hydrophila* infection and (ii) inhibition of the development of a disease caused by an *Aeromonas hydrophila* infection.

As used herein, the terms "treatment" and "treat" refer to all actions that (i) suppress a disease caused by *Aeromonas hydrophila* and (ii) alleviate the pathological condition of the disease caused by *Aeromonas hydrophila*.

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is typically used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may further include lubricants, wetting agents, sweeteners, flavors, emulsifiers, suspension agents, and preservatives, in addition to the above components.

The bacteriophage Aer-HYP-3 is contained as an active ingredient in the composition of the present invention. The bacteriophage Aer-HYP-3 is contained at a concentration from $1\times10^1$ pfu/ml to $1\times10^{30}$ pfu/ml or from $1\times10^1$ pfu/g to $1\times10^{30}$ pfu/g, and preferably at a concentration from $1\times10^4$ pfu/ml to $1\times10^{15}$ pfu/ml or from $1\times10^4$ pfu/g to $1\times10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multi-dose container.

Here, the formulation may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be provided in the form of a medicine bath agent or a feed additive depending on the purpose of use thereof, without limitation thereto. In order to improve the effectiveness thereof, bacteriophages that confer antibacterial activity against other bacterial species may be further included in the composition of the present invention. In addition, other kinds of bacteriophages that have antibacterial activity against *Aeromonas hydrophila* may be further included in the composition of the present invention. These bacteriophages may be combined appropriately so as to maximize the antibacterial effects thereof, because their antibacterial activities against *Aeromonas hydrophila* may vary from the aspects of antibacterial strength or antibacterial spectrum.

Advantageous Effects

According to the present invention, the method of preventing and treating a disease caused by *Aeromonas hydrophila* using the composition containing the bacteriophage Aer-HYP-3 as an active ingredient can have the advantage of very high specificity for *Aeromonas hydrophila* compared to conventional methods based on existing antibiotics. This means that the composition can be used for preventing and treating a disease caused by *Aeromonas hydrophila* without affecting other useful commensal bacteria, and has fewer side effects attributable to the use thereof. Typically, when antibiotics are used, commensal bacteria are also harmed, ultimately lowering the immunity of animals and thus causing various side effects owing to the use thereof. Meanwhile, in the case of various bacteriophages exhibiting antibacterial activity against the same bacterial species, the antibacterial effects of the bacteriophages are different with regard to antibacterial strength or antibacterial spectrum [the range in which antibacterial activity of bacteriophages is exhibited against various bacterial strains belonging to *Aeromonas hydrophila* species, given that bacteriophages typically exert antibacterial activity against some bacterial strains belonging to the same bacterial species, that is, susceptibility to bacteriophages varies even among individual bacterial strains belonging to the same bacterial species]. Accordingly, the present invention can provide antibacterial activity against *Aeromonas hydrophila* different from that of other bacteriophages acting on *Aeromonas hydrophila*. This provides a great difference in effectiveness when using industrial fields.

DESCRIPTION OF DRAWINGS

FIG. 1 shows an electron micrograph of the bacteriophage Aer-HYP-3.

FIG. 2 shows the results of an experiment on the ability of the bacteriophage Aer-HYP-3 to kill *Aeromonas hydrophila*. Based on the center line of the plate medium, the left side shows the results obtained using only a buffer not containing bacteriophage Aer-HYP-3, and the right side shows the results obtained using a solution containing bacteriophage Aer-HYP-3, the clear zone, which is observed at the right side, being a plaque formed due to lysis of the test target bacteria by the action of bacteriophage Aer-HYP-3.

MODE FOR INVENTION

A better understanding of the present invention will be given through the following examples, which are merely set forth to illustrate the present invention, and are not to be construed as limiting the scope of the present invention.

Example 1: Isolation of Bacteriophage Capable of Killing *Aeromonas hydrophila*

Samples collected from nature were used to isolate a bacteriophage capable of killing *Aeromonas hydrophila*. Here, the *Aeromonas hydrophila* strains used for the bacteriophage isolation were previously isolated by the present inventors and identified as *Aeromonas hydrophila*.

The procedure for isolating the bacteriophage is specified below. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Aeromonas hydrophila* at a ratio of 1/1,000, followed by shaking culture at 25° C. for 3 to 4 hr. After completion of the culture, centrifugation was performed at 8,000 rpm for 20 min and a supernatant was recovered. The recovered supernatant was inoculated with *Aeromonas hydrophila* at a ratio of 1/1,000, followed by shaking culture at 25° C. for 3 to 4 hr. When the bacteriophage was included in the sample, the above procedure was repeated a total of 5 times in order to sufficiently increase the number (titer) of bacteriophages. After repeating the procedure 5 times, the culture solution was centrifuged at 8,000 rpm for 20 min. After the centrifugation, the recovered supernatant was filtered using a 0.45 µm filter. The filtrate thus obtained was used in a typical spot assay for examining whether or not a bacteriophage capable of killing *Aeromonas hydrophila* was included therein.

The spot assay was performed as follows. A TSB culture medium was inoculated with *Aeromonas hydrophila* at a ratio of 1/1,000, followed by shaking culture at 25° C. overnight. 3 ml ($OD_{600}$ of 1.5) of the *Aeromonas hydrophila* culture solution prepared as described above was spread on a TSA (Tryptic Soy Agar: casein digest, 15 g/L; soybean digest, 5 g/L; NaCl, 5 g/L; agar, 15 g/L) plate. The plate was left on a clean bench for about 30 min to dry the spread solution. After drying, 10 µl of the filtrate prepared as described above was spotted onto the plate which *Aeromonas hydrophila* was spread, and then left for about 30 min to dry. After drying, the plate that was subjected to spotting was standing-cultured at 25° C. for one day, and was then examined for the formation of a clear zone at the position at which the filtrate was dropped. In the case in which the filtrate generated a clear zone, it was judged that a bacteriophage capable of killing *Aeromonas hydrophila* was included therein. Through the above examination, a filtrate containing a bacteriophage having the ability to kill *Aeromonas hydrophila* could be obtained.

The pure bacteriophage was isolated from the filtrate confirmed to have the bacteriophage capable of killing *Aeromonas hydrophila*. A typical plaque assay was used to isolate the pure bacteriophage. Specifically, a plaque formed in the course of the plaque assay was recovered using a sterilized tip, added to the *Aeromonas hydrophila* culture solution, and then cultured at 25° C. for 4 to 5 hr. Thereafter, centrifugation was performed at 8,000 rpm for 20 min to obtain a supernatant. The supernatant thus obtained was added with the *Aeromonas hydrophila* culture solution at a volume ratio of 1/50, and then cultured at 25° C. for 4 to 5 hr. In order to increase the number of bacteriophages, the above procedure was repeated at least 5 times, after which centrifugation was performed at 8,000 rpm for 20 min to afford a final supernatant. A plaque assay was performed again using the supernatant thus obtained. In general, the isolation of a pure bacteriophage is not completed through a single iteration of a procedure, so the above procedure was repeated using the plaque formed above. After at least 5 repetitions of the procedure, the solution containing the pure bacteriophage was obtained. The procedure for the isolation of the pure bacteriophage was generally repeated until the generated plaques became similar to each other with regard to size and morphology. In addition, final isolation of the pure bacteriophage was confirmed using electron microscopy. The above procedure was repeated until isolation of the pure bacteriophage was confirmed using electron microscopy. The electron microscopy was performed according to a typical method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a Myoviridae bacteriophage.

The solution containing the pure bacteriophage confirmed above was subjected to the following purification process. The solution containing the pure bacteriophage was added with the *Aeromonas hydrophila* culture solution at a volume ratio of 1/50 based on the total volume of the solution, and then cultured for 4 to 5 hr. Thereafter, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 μm filter, followed by a typical polyethylene glycol (PEG) precipitation process. Specifically, 100 ml of the filtrate was added with PEG and NaCl at 10% PEG 8000/0.5 M NaCl, allowed to stand at 4° C. for 2 to 3 hr, and then centrifuged at 8,000 rpm for 30 min to afford a bacteriophage precipitate. The bacteriophage precipitate thus obtained was suspended in 5 ml of a buffer (10 mM Tris-HCl, 10 mM $MgSO_4$, 0.1% gelatin, pH 8.0). The resulting material may be referred to as a bacteriophage suspension or bacteriophage solution.

The bacteriophage purified as described above was collected, was named the bacteriophage Aer-HYP-3, and was then deposited at the Korean Collection for Type Cultures, Korea Research Institute of Bioscience and Biotechnology on Feb. 7, 2018 (Accession number: KCTC 13479BP).

Example 2: Separation and Sequence Analysis of Genome of Bacteriophage Aer-HYP-3

The genome of the bacteriophage Aer-HYP-3 was separated as follows. The genome was separated from the bacteriophage suspension obtained using the same method as described in Example 1. First, in order to eliminate DNA and RNA of *Aeromonas hydrophila* included in the suspension, 200 U of each of DNase I and RNase A was added to 10 ml of the bacteriophage suspension and then allowed to stand at 37° C. for 30 min. After being allowed to stand for 30 min, in order to inactivate the DNase I and RNase A activity, 500 μl of 0.5 M ethylenediaminetetraacetic acid (EDTA) was added thereto, and the resulting mixture was then allowed to stand for 10 min. In addition, the resulting mixture was again allowed to stand at 65° C. for 10 min, and 100 μl of proteinase K (20 mg/ml) was then added thereto so as to break the outer wall of the bacteriophage, followed by reaction at 37° C. for 20 min. Thereafter, 500 μl of 10% sodium dodecyl sulfate (SDS) was added thereto, followed by reaction at 65° C. for 1 hr. After the reaction for 1 hr, the resulting reaction solution was added with 10 ml of a mixed solution of phenol:chloroform:isoamyl alcohol, which were mixed at a component ratio of 25:24:1, and then mixed well. Then, the resulting mixture was centrifuged at 13,000 rpm for 15 min to thus separate layers. Among the separated layers, the upper layer was selected, added with isopropyl alcohol at a volume ratio of 1.5, and centrifuged at 13,000 rpm for 10 min in order to precipitate the genome. The precipitate was recovered and washed by addition with 70% ethanol and centrifuged at 13,000 rpm for 10 min. The washed precipitate was recovered, dried in a vacuum and then dissolved in 100 μl of water. This procedure was repeated to thus obtain a sufficient amount of the genome of the bacteriophage Aer-HYP-3.

The genome thus obtained was subjected to next-generation sequencing analysis using an Illumina Mi-Seq sequencer from Macrogen, Inc., and then information on the sequence of the genome of bacteriophage Aer-HYP-3 was obtained. The finally analyzed genome of the bacteriophage Aer-HYP-3 had a size of 54,451 bp and the whole genome sequence is represented by SEQ ID NO: 1.

The homology (similarity) of the bacteriophage Aer-HYP-3 genomic sequence obtained above with previously reported bacteriophage genomic sequences was investigated using BLAST on the web. Based on the results of BLAST investigation, the genomic sequence of the bacteriophage Aer-HYP-3 was identified to have relatively high homology with the sequence of the *Aeromonas* bacteriophage pAh6-C (GenBank Accession number: KJ858521.1) (Query coverage/identity: 93%/97%). However, the number of open reading frames (ORFs) on the bacteriophage Aer-HYP-3 genome was 75, whereas the *Aeromonas* bacteriophage pAh6-C was found to have 86 open reading frames, based on which these two bacteriophages were also evaluated to be different.

Therefore, it can be concluded that the bacteriophage Aer-HYP-3 is a novel bacteriophage different from previously reported bacteriophages. Moreover, since the antibacterial strength and spectrum of bacteriophages typically vary depending on the type of bacteriophage, it is considered that the bacteriophage Aer-HYP-3 can provide antibacterial activity different from that of any other bacteriophages reported previously.

Example 3: Evaluation of Ability of Bacteriophage Aer-HYP-3 to Kill *Aeromonas hydrophila*

The ability of the isolated bacteriophage Aer-HYP-3 to kill *Aeromonas hydrophila* was evaluated. In order to evaluate the killing ability, the formation of clear zones was observed using a spot assay in the same manner as described in Example 1. A total of 15 strains that had been isolated and identified as *Aeromonas hydrophila* by the present inventors were used as *Aeromonas hydrophila* strains for the evaluation of killing ability. The bacteriophage Aer-HYP-3 had the ability to kill a total of 13 strains among strains of *Aeromonas hydrophila*, which was the experimental target. A representative experimental result is shown in FIG. 2. Meanwhile, the ability of the bacteriophage Aer-HYP-3 to kill *Edwardsiella tarda, Vibrio anguillarum, Vibrio ichthyoenteri, Lactococcus garvieae, Streptococcus parauberis, Streptococcus iniae,* and *Aeromonas salmonicida* was also evaluated. Consequently, the bacteriophage Aer-HYP-3 did not have the ability to kill these microorganisms.

Therefore, it can be concluded that the bacteriophage Aer-HYP-3 has strong ability to kill *Aeromonas hydrophila* and can exhibit antibacterial effects against many *Aeromonas hydrophila* strains, indicating that the bacteriophage Aer-HYP-3 can be used as an active ingredient of a composition for preventing and treating diseases caused by *Aeromonas hydrophila*.

Example 4: Experiment for Prevention of *Aeromonas hydrophila* Infection Using Bacteriophage Aer-HYP-3

100 µl of a bacteriophage Aer-HYP-3 solution at a concentration of $1 \times 10^8$ pfu/ml was added to a tube containing 9 ml of a TSB culture medium. To another tube containing 9 ml of a TSB culture medium, only the same amount of TSB culture medium was further added. An *Aeromonas hydrophila* culture solution was then added to each tube so that absorbance reached about 0.5 at 600 nm. After the addition of *Aeromonas hydrophila*, the tubes were transferred to an incubator at 25° C., followed by shaking culture, during which the growth of *Aeromonas hydrophila* was observed. As shown in Table 1 below, it was observed that the growth of *Aeromonas hydrophila* was inhibited in the tube to which the bacteriophage Aer-HYP-3 solution was added, whereas the growth of *Aeromonas hydrophila* was not inhibited in the tube to which the bacteriophage solution was not added.

TABLE 1

Growth inhibition of *Aeromonas hydrophila*

| Classification | $OD_{600}$ absorbance value | | |
|---|---|---|---|
| | 0 min after culture | 60 min after culture | 120 min after culture |
| Not added with bacteriophage solution | 0.49 | 1.06 | 1.57 |
| Added with bacteriophage solution | 0.49 | 0.27 | 0.16 |

The above results show that the bacteriophage Aer-HYP-3 of the present invention not only inhibits the growth of *Aeromonas hydrophila* but also has the ability to kill *Aeromonas hydrophila*. Therefore, it is concluded that the bacteriophage Aer-HYP-3 can be used as an active ingredient of the composition for preventing diseases caused by *Aeromonas hydrophila*.

Example 5: Animal Testing for Prevention of Disease Caused by *Aeromonas hydrophila* Using Bacteriophage Aer-HYP-3

A total of 2 groups of twenty rainbow trout per group (average body weight: 22.8 g and average body length: 14.9 cm) were prepared and farmed separately in water tanks, and an experiment was performed for 14 days. The environment surrounding the water tanks was controlled, and the temperature in the laboratory where the water tanks were located was maintained constant. Over the whole test period starting from the beginning of the experiment, a feed containing $1 \times 10^8$ pfu/g of bacteriophage Aer-HYP-3 was provided to rainbow trout in an experimental group (administered with the bacteriophage) in a typical feeding manner. For comparison, a feed having the same composition but excluding bacteriophage Aer-HYP-3 was provided to rainbow trout in a control group (not administered with the bacteriophage) in the same feeding manner. For 2 days from the seventh day after the start of the experiment, the feed was further added with $1 \times 10^8$ cfu/g of *Aeromonas hydrophila* and then provided twice a day, thereby inducing infection with *Aeromonas hydrophila*. From the ninth day after the start of the experiment, furunculosis was examined in all test animals on a daily basis. The furunculosis was evaluated by measuring the size of ulcers on the body surface. The size of ulcers on the body surface was measured according to a commonly used Ulcer Size (US) score (normal (no ulcer): 0, small ulcer (ulcer size: less than 0.5 cm): 1, large ulcer (ulcer size: 0.5 cm or more): 2). The results thereof are shown in Table 2 below.

TABLE 2

Results of measurement of ulcer size on body surface (mean)

| Days | US score (mean) | | | | | |
|---|---|---|---|---|---|---|
| | D9 | D10 | D11 | D12 | D13 | D14 |
| Control group (not administered with bacteriophage) | 0.35 | 0.50 | 0.55 | 0.55 | 0.65 | 0.75 |
| Experimental group (administered with bacteriophage) | 0.15 | 0.05 | 0 | 0 | 0 | 0 |

As is apparent from the above results, it can be confirmed that the bacteriophage Aer-HYP-3 of the present invention was very effective in the prevention of diseases caused by *Aeromonas hydrophila*.

Example 6: Treatment of Disease Caused by *Aeromonas hydrophila* Using Bacteriophage Aer-HYP-3

The therapeutic effect of the bacteriophage Aer-HYP-3 on diseases caused by *Aeromonas hydrophila* was evaluated as follows. A total of 2 groups of forty rainbow trout per group (average body weight: 23.2 g and average body length: 15.4 cm) were prepared and farmed separately in water tanks, and an experiment was performed for 14 days. The environment surrounding the water tanks was controlled, and the temperature in the laboratory where the water tanks were located was maintained constant. For 3 days from the fifth day after the start of the experiment, a feed contaminated with $1 \times 10^8$ cfu/g of *Aeromonas hydrophila* was provided twice a day in a typical feeding manner. Rainbow trout subjects showing clinical symptoms of furunculosis were observed in both water tanks from the last day of the procedure in which the feed contaminated with *Aeromonas hydrophila* was provided. From the next day after the feeding with the feed contaminated with *Aeromonas hydrophila* for 3 days (from the eighth day after the start of the experiment), a feed containing the bacteriophage Aer-HYP-3 ($1 \times 10^8$ pfu/g) was provided to rainbow trout in an experimental group (administered with the bacteriophage) in a typical feeding manner. For comparison, a feed having the same composition but excluding bacteriophage Aer-HYP-3 was provided to rainbow trout in a control group (not administered with the bacteriophage) in the same feeding manner. From the next day after the forced infection with *Aeromonas hydrophila* for 3 days (from the eighth day after the start of the experiment), furunculosis was examined in all test animals on a daily basis. The furunculosis caused by *Aeromonas hydrophila* was evaluated by measuring the ulcer size on the body surface, as shown in Example 5. The results thereof are shown in Table 3 below.

TABLE 3

Results of measurement of ulcer size on body surface (mean)

| Days | US score (mean) | | | | | | |
|---|---|---|---|---|---|---|---|
| | D8 | D9 | D10 | D11 | D12 | D13 | D14 |
| Control group (not administered with bacteriophage) | 0.85 | 1.05 | 1.30 | 1.55 | 1.60 | 1.60 | 1.70 |
| Experimental group (administered with bacteriophage) | 0.95 | 0.80 | 0.40 | 0.30 | 0.25 | 0.15 | 0.10 |

As is apparent from the above results, it can be confirmed that the bacteriophage Aer-HYP-3 of the present invention was very effective in the treatment of diseases caused by *Aeromonas hydrophila*.

Example 7: Preparation of Feed Additive and Feed

A feed additive was prepared using a bacteriophage Aer-HYP-3 solution so that bacteriophage Aer-HYP-3 was contained in an amount of $1\times10^8$ pfu per gram of the feed additive. The feed additive was prepared in a manner in which the bacteriophage solution was added with maltodextrin (50%, w/v) and then freeze-dried, followed by final pulverization into a fine powder. In the above preparation procedure, the drying process may be embodied as drying under reduced pressure, drying with heat, or drying at room temperature. In order to prepare the control for comparison, a feed additive not containing the bacteriophage was prepared using the buffer (10 mM Tris-HCl, 10 mM $MgSO_4$, 0.1% gelatin, pH 8.0) used in the preparation of the bacteriophage solution, in lieu of the bacteriophage solution.

Each of the two kinds of feed additives thus prepared was mixed with a raw fish-based moist pellet at a weight ratio of 250, thus obtaining two kinds of final feed.

Example 8: Preparation of Medicine Bath Agent

The method of preparing a medicine bath agent was as follows. A medicine bath agent was prepared using a bacteriophage Aer-HYP-3 solution so that bacteriophage Aer-HYP-3 was contained in an amount of $1\times10^8$ pfu per ml of the medicine bath agent. In the method of preparing the medicine bath agent, the bacteriophage Aer-HYP-3 solution was added so that the bacteriophage Aer-HYP-3 was contained in an amount of $1\times10^8$ pfu per ml of the buffer used in the preparation of the bacteriophage solution, and mixing was sufficiently performed. In order to prepare the control for comparison, the buffer used in the preparation of the bacteriophage solution was used without change as a medicine bath agent not containing the bacteriophage.

The two kinds of medicine bath agents thus prepared were diluted with water at a volume ratio of 1,000, thus obtaining final medicine bath agents.

Example 9: Confirmation of Feeding Effect on Rainbow Trout Farming

The improvement in rainbow trout farming as the result of feeding was evaluated using the feed and the medicine bath agent prepared in Examples 7 and 8. In particular, the present evaluation was focused on mortality ratio. A total of 200 rainbow trout were divided into two groups, each including 100 rainbow trout (group A: fed with the feed and group B: treated with the medicine bath agent), and an experiment was performed for four weeks. Each group was divided into subgroups, each including 50 rainbow trout, and the subgroups were classified into a subgroup to which the bacteriophage Aer-HYP-3 was applied (subgroup-①) and a subgroup to which the bacteriophage was not applied (subgroup-②). In the present experiment, the target rainbow trout were 5-week-old rainbow trout (average body weight: 23.2 g and average body length: 15.4 cm), and the rainbow trout in the experimental subgroups were farmed in separate water tanks placed apart from each other at a certain space interval. The subgroups were classified and named as shown in Table 4.

TABLE 4

Subgroup classification and expression in rainbow-trout-feeding experiment

| | Subgroup classification and expression | |
|---|---|---|
| Application | Bacteriophage Aer-HYP-3 is applied | Bacteriophage is not applied |
| Group fed with feed | A-① | A-② |
| Group treated with medicine bath agent | B-① | B-② |

In the case of provision of the feed, the feed prepared in Example 7 was provided in a typical feeding manner as classified in Table 4. The treatment using the medicine bath agent was performed in a typical treatment manner of immersing fish in a diluted solution of a medicine bath agent as classified in Table 4 using the medicine bath agent prepared as described in Example 8. The results thereof are shown in Table 5 below.

TABLE 5

Mortality ratio in rainbow-trout-feeding experiment

| Group | Dead rainbow trout/rainbow trout of experiment (No.) | Mortality ratio (%) |
|---|---|---|
| A-① | 4/50 | 8.0 |
| A-② | 10/50 | 20.0 |
| B-① | 6/50 | 12.0 |
| B-② | 17/50 | 34.0 |

The above results indicate that the provision of the feed prepared according to the present invention and the treatment using the medicine bath agent prepared according to the present invention were effective at reducing mortality ratio upon rainbow trout farming. Therefore, it is concluded that the composition of the present invention is effective when used for feeding of rainbow trout.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Name of Depositary Authority: KCTC
Accession number: KCTC 13479BP
Accession date: 20180207

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

RECEIPT FOR ORIGINAL DEPOSIT
issued pursuant to Rule 7.1

NAME OF DEPOSITOR: iNtRON Biotechnology, Inc.
ADDRESS: 137 Sagimakgol-ro, Joongwon-gu, Seongnam-si, Gyeonggi-do, Republic of Korea (Postal code 13202)

| I. IDENTIFICATION OF THE MICROORGANISM ||
|---|---|
| Identification reference given by the DEPOSITOR: Bacteriophage Aer-HYP-3 | Accession number given by the INTERNATIONAL DEPOSITARY AUTHORITY: KCTC 13479BP |

| II. SCIENTIFIC DESCRIPTION AND PROPOSED TAXONOMIC DESIGNATION |
|---|
| The microorganism identified under I above was accompanied by:<br>[ ] a scientific description<br>[ ] a proposed taxonomic designation |

| III. RECEIPT AND ACCEPTANCE |
|---|
| This International Depositary Authority accepts the microorganism identified under I above, which was received thereby on February 7, 2018. |

| V. INTERNATIONAL DEPOSITARY AUTHORITY ||
|---|---|
| Name: Korean Collection for Type Cultures<br><br>Address: Biological Resource Center in Korea Research Institute of Bioscience & Biotechnology (KRIBB) 181 Ypsin-gil, Jeongeup-si, Jeollabuk-do, Republic of Korea (56212) | Signature(s) of person(s) having power to represent the International Depositary Authority or of authorized official(s):<br><br>Representative<br><br>February 7, 2018 |

BUDAPEST TREATY ON THE INTERNATIONAL
RECOGNITION OF THE DEPOSIT OF MICROORGANISMS
FOR THE PURPOSES OF PATENT PROCEDURE
INTERNATIONAL FORM
RECEIPT FOR ORIGINAL DEPOSIT
issued pursuant to Rule 7.1
NAME OF DEPOSITOR: iNtRON Biotechnology, Inc.
ADDRESS: 137 Sagimakgol-ro, Joongwon-gu, Seongnam-si,
Gyeonggi-do, Republic of Korea (Postal code 13202)

I. IDENTIFICATION OF THE MICROORGANISM

Identification reference given by the DEPOSITOR: Bacteriophage Aer-HYP-3

Accession number given by the INTERNATIONAL DEPOSITARY AUTHORITY: KCTC 13479BP

II. SCIENTIFIC DESCRIPTION AND PROPOSED TAXONOMIC DESIGNATION

The microorganism identified under I above was accompanied by:
[ ] a scientific description
[ ] a proposed taxonomic designation

III. RECEIPT AND ACCEPTANCE

This International Depositary Authority accepts the microorganism identified under I above, which was received thereby on Feb. 7, 2018.

V. INTERNATIONAL DEPOSITARY AUTHORITY

Name: Korean Collection for Type Cultures
Address: Biological Resource Center in Korea Research Institute of Bioscience & Biotechnology (KRIBB) 181 Ypsin-gil, Jeongeup-si, Jeollabuk-do, Republic of Korea (56212)

Signature (s) of person (s) having power to represent the International Depositary Authority or of authorized official (s):
Representative
Feb. 7, 2018

The invention claimed is:

1. A method of preventing and treating a disease caused by *Aeromonas hydrophila*, comprising:
   immersing an animal other than a human in the composition comprising, as the active ingredient, a Myoviridae bacteriophage Aer-HYP-3 (Accession number: KCTC 13479BP) having an ability to kill *Aeromonas hydrophila* and a genome consisting of a sequence as set forth in SEQ ID NO: 1.

2. The method of claim 1, wherein the composition is in a form of a medicine bath agent.

3. A method of preventing and treating a disease caused by *Aeromonas hydrophila*, comprising:
   administering to an animal other than a human the composition comprising, as the active ingredient, a Myoviridae bacteriophage Aer-HYP-3 (Accession number: KCTC 13479BP) having an ability to kill *Aeromonas hydrophila* and a genome consisting of a sequence as set forth in SEQ ID NO: 1.

4. The method of claim 3, wherein the composition is in a form of a feed additive same as an active ingredient.

* * * * *

SEQUENCE LISTING

```
<160> NUMBER OF SEQ ID NOS: 1

<210> SEQ ID NO 1
<211> LENGTH: 54451
<212> TYPE: DNA
<213> ORGANISM: Bacteriophage Aer-HYP-3
<220> FEATURE:
<221> NAME/KEY: misc_feature
<222> LOCATION: (13443)..(13443)
<223> OTHER INFORMATION: n is a, c, g, or t

<400> SEQUENCE: 1
catcatcctg aaccagacca ctccggaagg tcaggaaacc gtacgtatcc gtgagaccct      60
gccgctgcag ttcctgccgg ttcagctcca cggtttggtg tacgaagttc cgggtcgtgg     120
ccgcttcggt ggtctggaag tgacctaccc gcgcgccatc gacatctggt acggcctgta     180 atacccgta actgagggct ccggccctct aatttggaga agataatgca agttcaaaac      240
actactgatc actacatctc tttcgttgct cgtaccaatc ctggtgccaa gaccaaaggc     300
tacgacccac gtggtaatga aatcatgcgt gacgagctgc cgcagctgcg tactgtgacc     360
atccctggtg gtgccactgt cgaagttgac gatgcactct ggaacgctgc taccagcggc     420
aagcctgcca cccgtcaagg tatcgagatg gaaaaggtgc cggtacaact gggttccgac     480
gatccgtcca aggaagccaa gtaccacgtc ctgaacccg tgggtgacgg caaggtggtg      540
cacttcaatc cggtcatgga gctggtgcga gccggtgatc tgaagatcgt agagcacgcc     600
aagtctgaac tgactctgga agatctgcgg aaggcagttg aactcgctca aggctacgcc     660
ctgcccaagg aagtagacga agagaaactg cagcacatgt acaacgtgct ctgtaagtaa     720
ggacaatcaa tgctcaccta cgattcgtgg ctggacaagt tcccgcagtt cgtagctgtc     780
tctgagcctc aatgggcaga gctccagctc gaagcaaccg tagaaatggg cgccgatgtc     840
```

-continued

```
tttcgttgga atggccaaga tgcgtacgat attgcccaag gctatctgat ggcgcatctt    900
gctgctcaag cagaatcgaa cgaggcgggg gaccacaccc cgctccaacc gttccgcgag    960
aaagaagttg atgatgtgcg agtcgagtat gcagtgtcga gagatatgca gaataacctc   1020
gacccgtatc tggctaccag ctatggtcag cagtacatca agtggcgacg catggcattt   1080
gctggcccac gtgtgatttg aggttactat gatctcatta gcaccagctt ttggatcgca   1140
caccactact caggtgatgt tgcggttgga aattccaggc cagtacgatg gcgacaacat   1200
ctggattact ggtggttatg gtttagcctt tccaataagg gctacgccaa tcccactagg   1260
tgatccagat tacggcgact acggtaaggc tctgaagtcc gacccgtctg cgaacggca    1320 accagctcaa atcaagattg catctcgatg gaagctgccg aacaattccc tgatggaata   1380
cggaactgag ttgtacaaga taatccggga aggtgactac cactccgcag gttctggca    1440 ggccattggt gccacagata ccacactgca tccggtagtg ccgctggatt atccaagtga   1500
tatgatgctg atgtacggca acaagctcgt accagtgtcc cgaatcataa ggccaaggta   1560
tggaaaaagc gggtgatacc cttcgagcta tgaagctcgt ggacctcgct ctgggcaagc   1620
caaagttctc ctatgagatg aagcgcaacc agcctaagcc gaaggtcgac agctttgcag   1680
ctgtgctcct gctcgacgag cgtaatccag gccgtgacag gaacgaagtc attgagactc   1740
caactggatt tatcaaccgg acgtctggag ttcggttggt agtgtttcaa atcttgttca   1800
ccgaaggcat cccagatgtc tctcgattcg tctccagctt tatgcggcct gacgtgcagg   1860
acttcatggt agagaacgat ctcgccgtgt tgaagcacga gaaggtaacg aacaagactc   1920
tgatccttga aaccaactgg gaagtgcgcg agagcgtatt aatcgaatgc ctggtacgcc   1980
ggtcgttcga tagcgagatt ggtatcatct ccgaggtaga tgcaaatggt atctacaacg   2040
agggtgatat gacagtcccg atgcatatca atatcaagga accttgatga gcctttcaat   2100
cactaatgtt gttgacgtca acatcctgat tgccccgaaa gctaaagccc tgcaaagctt   2160
cggcaagctg gtattcgtca ccgacgaaag cccgaaggtg cccctcgctg gtaccatctt   2220
ctcctactct ggcatcgaag ccgtagcaga tgaatgggaa ctgacctctg aggtctacaa   2280
gggtgctacc actttctacg gccagaaccc gagcggttcc ttcatggtcg cgctggcagc   2340
tgctgctact ccggctgttc tgaccggcgg ctccgccgat ctggcagaca tccaggccat   2400
caccgctggt ggctttacca ttcacgtgaa tggcatggct cagaacatca ctgatgttga   2460
cttctccggc gcgtccacac tgaccgctgc cgctgccatc ctggaaggcg agctgactgg   2520
cgttgacgtg accgtgtctg gcaccagctt cgtgctgacc acccagacca tcggtaccgg   2580
tgcgtccatc tctgtggcca ctgccgacat atccggcact gccgccgcac tggcgctgac   2640
caccctgacc ggtgctgtcg tgactgctgc cgttgtgccg gagtctcctg tggaggcact   2700
gaccaaggcc gccgacactg atccgtcctt ctacggcatc gtgctgaaca agaagtggcg   2760
cgacaccgcc caggccattg acaccgccga gtatgctcag gcgtcccgcc gtgtgttctt   2820
caacacctcc aacgaccctg ccactctgga caagaccagc gaagacagca tcgcgtacaa   2880
actgaaaggc atgtccattc agcgcgtgct gactcactac agctccaagc ccaacgagta   2940
cccgtcctgt gcgcgttgctg gtcgtgcttt cctggtgaac ttcgaaggca ccaacaccac   3000
cattaccctg aacctcaagg tgatgaaggg cgttaccttc gagaagctgc gtcagaccga   3060
gcatgaagca atgcaggcga caactgcaa cgccatcgtt gacctggccg gtgcattcgt   3120
atactccgac tcccgcatgg gcgacggtac ctggttcgat gctgttcacg gtgtggactg   3180
gctgcagaac cgtatcgaga ccggtatctt caatcggatg tacaccactc cgaccaagat   3240
```

```
cccgtatacc gataccggtg tcaccatcat catcgccgag atcgagcagg ccctgcgtca    3300
agcagtgacc aacggtctgg ttgctccggg caataccacc tctggtgagt acctcccgct    3360
gggttacaag atcgtgtaca ttccgactgc acaagtgtct caagccgaca gtccaaccg     3420 tgtctacaaa ggtatcacct ttgaagccgt tggtgccggt gcgatgcaca aggtagtagt    3480
tggtggctcc ttcaacgaat aaggataacg atgaaacagt atagctttta caacgtcgat    3540
cttctggtcg acggtatcct catggaaggc ttctccgact ctgccgcaat catcaccgcg    3600
tctcgtgacg caccgcaaca cggtaaggtg atggatgcgc gtgggaagat ggttgcgatt    3660
acctcagctg acaagtctgg taccgtaacc ttcgacctgc tgcaagtctc tgattccaac    3720
cagtggctgc aggttcgtgc catgcagacc cacgacgccg gtacttccgg tggcactgac    3780
gtcttcctgc cggtgcagct gatgatgaac gataagatgg gtcgcgctgt cgtgaccggt    3840
gttaacggca tcatcaccat gcagcctggt atcgttcgtg gtaccggtgt agcgaccgac    3900
acctgggtta tgcagttcga gcaactgtgg atcctgcgcg tcagtccga gaacgtcggc     3960 gtctaaccaa catacggagt aaccaatggc ttgtaaagac atgaatcggg ttatcgatga    4020
taatccgatc tatgttcgtc aatggccggc atctgtagcg ttggagaatt taagtgaggc    4080
gttgggcttt atgggccccg acttctcttt cttcgtcgac ggatcctacc aattcacgga    4140
catgctgcaa gtgctgcacc gcagcgattc caagcggctc gttgcactgc tgaagaagtt    4200
tgctatggcc gctcgtgtag acggtaaaga gctgcaagaa gcgcagttca accagtacta    4260
cagcggggag atcttcaaga tcttcaaggt attcgccttc gtagcagaag ttaactaccg    4320
agattttttc gagctagggg tacctccagc agagccagac cagcaggaag agcaggacga    4380
gtcgcaagac ccgcagccgc cagcgccgag cttgaccct tagaagaaaa gccgaagacg      4440
ctcgaagagc tgtttcctga ggttgacttc tacttgtatc ggggtgtaat ttgccatccg    4500
cctatgtgct caatgagtga tctgtcggat ggatcattat ctctgtatga cctccatatc    4560
atgcacgaga taatggacct gaaacaagaa ctgaaacaag gagacaaaga tggctaagcg    4620
cccaaccctt tcgattcccc gcaaggcgaa gcacaaaggg cagatgcaga atccgatcaa    4680
tgactttaaa gctgcaaaga gtagtcactc ttatgctgct gcccagtttg acattccaca    4740
aaagccggtg tcaaaaccgc tgcagcgtaa gagtgcctca ttctgggatg atggagaagg    4800
agaggactat gttgagcgca ctatgggcg acccactgag tccatccact ctgaagagta     4860
catcgcacaa gcaactacgc cggaacaaat cctggcgagt cgtatcaacg cggctggccc    4920
tgatgtagca tcggcattca tgtcgcatgt tgccaaggct aagtccctgg ggtcggtaga    4980
ccatacgggc ttcgcgatga gctccaatcc agctgagagg ctgcaataca tggcagggca    5040
aggaggcatc aacctccaga aagtagcatc agctatgcgg cacagggaca agcagtgggg    5100
atcacctgct gcggagggtt cccacgagga agacttctct gtacgtatgg ttgaggctgc    5160
gaagaccaga gcctaccaag gcctgcaaag cccgacacaa cgcgccatgt caatcgtagg    5220
cgcgatgacc accagtgacc agtcctggaa gcagcaagtt gatgctccag atctgataac    5280
ccctgacacc cacgacaagt gggtagaccc tctacagaag gctgtcaacg cggttcagtt    5340
catagctggt gcgtatattg atccgaacaa gctggaaggt ggtgagttcg acctgcctta    5400
cgccgatcta catgggcgcc ttactaaggt gctctcaagg caaataccctg cacggatagc   5460 gaacactggc ttcgagcaag ccacgcgtgg tgctggtagt aagcctgtag ttgacccca    5520 agccttgccg tctgtacagg acgtccgtaa gatgctgccc gtgtctgacc ggatgttcct    5580
```

```
caccaacaag ctggataagc tgtgggagga gaagaatggt cgacatgagt caccgttcac    5640
agacgcgatc aagaccatcc gagacgtgta ccgttctggt aacgagggtg gtctgtccaa    5700
gccgaagaac ttcgagtacc gtgagcggca atatctcctt gacgagatgg ctgcatccgg    5760
acttgtagac ccaacccaga ccgtcatttc cagaaccct ggacgagacg agatgtatga    5820
cttcaaggtc actaccgatg gtggtgagct gatgaactct gcattgcaag cgctgggtgc    5880
aactgccgct gacctcgttg gtgaccctgt catccgggct caagtaaagc gtgctgctgc    5940
tgaaatagct gcaactggtt ctgcaagtac cactgggact gttggagaca acctgacacc    6000
gaaggctgcc ctgctgggta tgcgtgactt cggtggaggg cctatcccgt tccagctgga    6060
gccgtacaag aagttcgagc gtggccgtgg tggtggcgcc accaccagga agaaaaaccc    6120
tgtagcacct gctggcatca agcctggtga tgtaatccaa acagcagcag aggcccaagc    6180
agaagtacgc caacgcactg gtgaccctga cggagccaga gcaaagtatt tcgcagagcg    6240
gccgtggttg aaagccatcg catcggatga tgacaaatca gacccgatgt cggcatggca    6300
gcgcaatcgt cgtggcaaag tgacctcatc cgccgcaggt gccttggcag acccagagtc    6360
tgcaagagga gctttgcatg cagtggtgaa gggggcgctg accaatccca acgacccagt    6420
gtctattggc cgaggctcta tctggactaa gtccggtgat gccctcgaac cagtggcact    6480
ggactggtac cgtaagcacg tcgaccctga tgccttgaa cctggtctta tctttaaccg    6540
gaacaaggct ggacaggcaa ctactcctga tgctattgct gatggtggtc gccgtaacgt    6600
agaagtgaag tctcgcaaca aattcattga ccccaacaac ccgttggatg ctaatgaagc    6660
gaagactctg cggaagaact acttgcagat gcagcaccag atgtacctca ccggtgcgtc    6720
cagtactgac cttgtcgaga tcctcaggga ccaagagaac cccaatgccc ctctgggcaa    6780
gaacggcctc aacgcaacaa catccgtaa gcgccgtgta accgtgatg acgagctcat    6840 ccggcagatg cggccgcaat gggaaacggc aggaaaggca gctgacaaga tcgcaggcct    6900
gaatgaccgt acccagaaga tgttcgccaa agcagtggaa gaaggtaaca ttcagtcctt    6960
cgagaagctg tccaaacgtc acgggattga aggccatgaa gcactcgcag caacgctcgg    7020
gctggcggaa ggcaagggta gtggcggtgg tggcggcggt ggagacaatt ctcgaccgta    7080
ccgtggaaac tacggcgggt tcggcggtcg tgatgctcct actactcttc ggggtggtgt    7140
gcgtggtggc ttagctgcca tgggtcgacc tggtaagatg ctcaacgtag ctcttgctgg    7200
tgctgaaatc ctctgggaca cagcgaacga catcaacgac acaggcctga atctatctgc    7260
gcaagcacgt gcaactggca tgcgtgaaga cttgttccgt aagacacgac tgagtatgac    7320
ccaaggtaaa taccttgatg atgcctcagc aatgtcggac atgtcatcta tcgcgcttgc    7380
caagggaggc ctgaacaggg gtttcactga ccgtgctgta aacttggtca ccagtactcg    7440
tggtgccatt actctaggtg acttgcagaa tacaaacctg caagacccgg atgccatcag    7500
aaacctgatg agtcagacag aaagccgtct tcgccgccga ggcgtaagtg aattcggcat    7560
cgcagctact atggaacagt cagggctgaa gtccttactg agtgccactg atgctgctgg    7620
tggtcgtgag tcgttgaaca acgcagtcac gaacatcaat gacaatattc tggaactgaa    7680
gctgacagcc ggtgattacc tggggcagat tgcaggattc ggggaagagt acttcaaggc    7740
catgagctca gcattgcagg acattgctgg ggtgctagcc ccaaatgctg gtggtggtgg    7800
agctcttgtc gaaggacgag ttcctatgtc aacgaccaga gacggtgtca ttggccctgc    7860
catccagtca gccattgatt cagtgactga cttcgccttg cctacaaggg caggtgaact    7920
ggccgacgag atctcattgt tctctggtat gaacggcacg ctacctgagg ctaacagggc    7980
```

```
ggcactcgag aagcaattcc gaggcatctc tgcatctcag cgcaacaggg taatggatgc    8040
aatccgcaac gactccttgg ataccaatca actggccaag acgttcgtg gtggtggcaa     8100 gctagaagtg gagctcaaga ctgatggtat ctctctgact gtgaaagacc agtccggacg    8160
tatcacttcg aaggctttca aaccttatca aggcggagcg gaataacatg ttcggtcgca    8220
ttatgcggtt ggaggcgagg cgggagctca cggcagaccc gttcttcgtc acagacaagc    8280
tgcgcattaa ctgcgaaatc gaaatgtcgt tggcgcagca actggccaa gccagtatca     8340 ccatctacaa cctgtcagaa gagaactcaa aagctctgac gtcaggtgac catgaggtgg    8400
cctcgaagga caatgctgag tcactgcgag tggcgtctaa agtctttatc cggctctatg    8460
ctggatacca agacgagatg ctggcgaacg gtgaactgcc attggtgata gagggtattg    8520
ttatgaacgc ctacgcgcgt cgtgcagtac cccaccacct cacgcatcta tttgtactgc    8580
cgttggcaag ctcgttcctg agacagccat tcacaccgtt ctctgtgcct cgtggaactc    8640
ccctgaggtt tgtgttggag cggatgacgt gggaggccgg cttttgaagcg gtgacgtttg   8700 atctgccgga ctccatcctg cagcaagaca tgggtggaga agctcttgag ccggaccctg    8760
acttgtacgg cacattgcac aagctaggaa aggcgtattc gtttactttc tctcaaagag    8820
caagtggcat tgggttctac ccgaggatcg acgatagcgc gcagagccac aacgagttca    8880
accatttgca ggctaacgga gaagtctaca acgtcaagcc attcttgctg aaaggcgcac    8940
ctactgttgg tgttgccacg atcagcttcc cgatggtgtt agacgccaaa gtattcccag    9000
gctgggtgat cgatgtccaa gacatctccg gcactgcagg tgacttggcg ttaccctcag    9060
gtggcttgcc tgactactct gcgcttggtg accgttgtt ctacacggac gacgttgcca     9120
agtacgcagt gctaccacgg tacatgctaa agaaagtcat ccacaagatg gacacctacg    9180
tcgacttgtg ggagacacta gtagttggga ctgttccgac tgctggtgat tatggaaagt    9240
gggagcaaca tggctaacaa actcagagac acaatgatca tctgggagga agagcccgga    9300
tcaggcaagt ggagtgtact cgcatttgac ggtgtagttc gtgaaggtca cagtggggct    9360
gtccaggtaa ctggctatcc tgtggactca ggcttccaag tctcggacca cgccatacgt    9420
cagaaccgta tcatcacact agacaccatc acctcgaata tctcaatgtc agtagctact    9480
agccgcaaga cattcgaaga gtcttttcaat gagctgatgg tggccattgg ctcagctcag    9540
acaggcggtg gtgcaccagt atatgatgct ggagaggtgt tcgacccaga gcaggagata    9600
gcttcagctg ccctgcgta ctccgagacc accaaatacg gtcgcgccgg ttacgacaac     9660
gacgctatca atatcaccat cccgtacacc agcattacac ttgggacgat taccaacccg    9720
attgcaacag cgttactctg ccaagtctct atcgacaagg tggacgaagc gctgaacaca    9780
gtcgacaggt tgaacgccct tggcaagctg gtgcatgtgg tgactctgcg tggtgttcgt    9840
aagaactgtg ttatccgcca gtacgatgca atcaacgatg tgaccaactc ctactcagtg    9900
cctatcgcgc tgacactgga gcagatgaac gtggttgacc tgactcgtag tactgtgcag    9960
gtaagtacca actacagtaa cggtgaagtg gtagctcaag agcaggccac tgtccggcga    10020
gtagtccctg aggctgcaac ggtagagaac gccatcaatc cagcggctgt acagctgttg    10080
gctgcaccgg tatctcgtgc ggttcaagct accgctatct ctgacggtga agtaccagac    10140
attgttccgg catcgttcta cgagatggaa caccgtgaag taccattctc cactgggttt    10200
gacactcggt tcatctacga gggcacagag tacacacttg aagagtgcg gtacaacgtg     10260 actctcggtt gctttgtgac tatcctgcaa tggcggaaag acggaaagta cgagaccatt    10320
```

```
gcaagcctgc cgttgcagag cggggtgaat ctcgttaggc agtatgccac caacatgccg    10380
tcattcgtag ctgtgaatac tcaggagcgg aacagcgacc cgtcagcacc agagaacctg    10440
cgactgtata tcatcaaagg gttcgatgaa acattcttag gattgtaatg gacgtcaaga    10500
cgaagacaat tgggactatt gtgtccttcg acccagaaag ccagatggct acggtcaagc    10560
tggcaaccaa cggaaccaac agtactctcg acaccaacta cttcaaccaa gaagggttga    10620
cgctgataga cgtaccggtg gaattcccaa ggtgtggtgc gttcgtaatg acgttccctg    10680
tgaatgcggg agatgactgt atcgtagagt tctatgagtc tggaatagac cactggctct    10740
acgagaacag acgggcgtac aatgtcgtaa atggccggtc agagccagca gcacgcaggc    10800
ggtatagccg taaagacgcg tcctgccgag tggcaatcga caacctcgcc aaccctattg    10860
gtgggttcaa tacctctgga cttgaaatca ggcatcgtaa cggtaaccag aagatggtat    10920
tccatccgga tggagtgatt gaaacgatca gtccgtctga catcaagttc atagccggtg    10980
gagacatcac ctttaaggct gacggaaata tcggtcttga gggctcgaat atcgagtcca    11040
cagccacggg ttcaaccaa gtgaaaggca caagcgtaac actgaagggc caaagcatct    11100
cgatggagca ataatgccag ccgtactcac gcatgtctca agaccagtg ggcacgatgg    11160 attccctcct acccagtcta agggcggtaa ctcgttcgta ggcattggag gtcatccggt    11220
tatactggta ggccaagaat tcgaaccgca ctctaacggt agtactcaca caccgaagct    11280
gattggcggc tcctcgttca tcaaggtgaa cggagtgcct gtcggactag tcggtgataa    11340
acttgattgt ggcgacacgg tcattgagag cgctactagt ttcttcacag caggaggctg    11400
aatgagtttc aatctcaagc tcggtgcaga ccacgatatc atcgttggga gacaggtctc    11460
gagaaccgat aaactggagt acactgtcca gcttgtcaaa tgcaggctcc ttacctttct    11520
tggtgagtgg gccttgaacc gaggaattgg tgtgccttgg actggagtac tggacaggtc    11580
ttacgacatc tccgcgacga agttcgcaat ccagaacact atccagacca ccgtgggtgt    11640
taagtcactc aattctttat ctctgaaagc ggacccaaca acgcgtctgt tgactgtaga    11700
attcacggcg acgtcgatct acggtgaaat tagcgcagga gtaacggtat gaccggtatt    11760
accgaagctg gaatcacggt caagacttat gacgagtgcg ttcgcagtct cgaacaaaga    11820
ttcaagctgg agtttggcga ctcgttcgac acgactccgg aaagccctga tggccagaac    11880
atcaggataa tggcagcatt catctacgat cagtggctgc tggccgagca agcgtaccac    11940
agttacaacc cgtccgtagt gaccggtact ggactggaca accttgttcg gctgaatggc    12000
ctgactcgta tcgtcgatac tccgactcgt gtcggtgtgt acttcgatgc tactactagt    12060
gctggtgagg ttctccctgc tggtactgtg gtagagaccg ccactgacaa aattcaattc    12120
gttaccactc gcagcatcat cctgcctggc gaagtgatcg cgtcgtgcct taccaaaggc    12180
gccatcacga tcttcccagg tgaggtcacg gtgattgcag acgatgtagc ttcagacatc    12240
actgtaacca accctgctgc tggtataact ggcgtagtac gtgagacaga cccgcagctt    12300
cgtgcgagac gggaacgatc actggtacgc gcagggacag cgactgctga ggcaatctac    12360
tcagccgtaa ctgacctgaa cctaagcttt attgcagtgc tggagaatga tactgatgct    12420
gttgttgatg gtattcctcc tcacgcattc aggacggtgg tcgagggtgg tgcgctggaa    12480
gacgttgctg agcgggtcta tcggaacaaa gcgataggca tccaagccta cggggacgtg    12540
aacattgaga tcactgactc cagaggctat cctcacatga tcggcttgtc ccgccccaac    12600
caagtaccca tctgggtaaa ggtgaaggtg aagcgaccga gcaacgttgc catcaacagc    12660
ctgcgtgaca tccgtgacgc catggtggaa cacatcaacg gcctgcaaat cgctacggac    12720
```

```
gttgaatggg gcaaactgta cgcgccagcc accaatgctg ctccagcagt gaacgtcaag    12780
ctcatcgagg tgagtaccga cggcgtgacg tacgtacagc aggacatcct gatggggcct    12840
gtcgacaaag ccaaaaccga cgagatcaag gtggtggtcg aggagttgcc atgagcactg    12900
taatcgcagc accgctgacg aagcttatgg acctgctgct gatgcagtac aggaactccc    12960
cgaacttcat caagtacctc tcttgttact ccgctgagct gcaagaggta tacgcgtgtc    13020
tacaacagga aatcactgac cgttactacg atgtagccgt tggtgctcag ttggacgtca    13080
tcggggatat cgttggggca ggcagaacgc tagaaggcgt gtcggtagct ggcaacttcg    13140
gctaccttga ctctgctgaa agtcttggta tgggtcgtga agacaacccg aatatcgggg    13200
gtcctttccg ctctgaggaa gacgacaccg tccaagacat caggctcaat gacgagcttt    13260
tccgcaactg gattgaggct cgaatcatca agaatcgtac cggatgcaat actgaagata    13320
ccatcgcgtt cttcacgctg ctcctgaacg acgacgagct tgacgtagag atcacaactc    13380
cagctccagc aacaacgaaa gtgagtctca agaagaccct cacaatctac gaggcagcgc    13440
aantcagaag tctcgcgcag catatcaagc ccgtaggtgt gactttcatc gttgaagact    13500
tcactggtgt cattgagaca ctgccaattg caagggtggc gtaatgacgt tgagaccggt    13560
gctcacgaaa ctgtgggcag aagacgcact cccagagaat ctcggcgacg ctggcagtta    13620
cattccggca aacccgagtt accccgatca gcagccgaac cagtatgctg taggctggac    13680
tgtgaaccac ccagtggtga agcagccgca ccattggatg aactcttggt tgtactcaac    13740
cgactggcag ctgatggagt ggtacaagtc gaatttcagc tggcaacaag agatcacgta    13800
cgttcaaggt gctgtgatta ttgttgacgg agttcggtat gtggcccaaa gcagcaacac    13860
caacaaggca cctctggcac atccagctat ctggttcccg gcaaagttcc atactatgct    13920
gcaagcccag gcagactacg cggcagtagc cctcaaggtg aataaccacg taggcgacaa    13980
tgacaacccg catggggaga cttacgagtc tttcaacggg atgtctcggg ctgacatcga    14040
cgcggcagta caggcacaag acacactggc acagaaccac atcagccgca tggataaccc    14100
gcatgggctg actccggcgg atgtgaatgt actcgacaaa gacatcggtg gcacattcac    14160
cggccaggtg gctatgacgc gaatagacgt cagtggtggt ggtatccgac ggctttccca    14220
aggattcgag atattcttgg atgctggtgc aaggctgggt attgacacca ctaagatgat    14280
ggcacagaaa gatgggcagg aaatgctctc tgatacgaac tacgcagctt ttcgcttgcg    14340
gaattccgat ctgttcaagc caccattgcc agaccttgac atgcctcttg gagccggatt    14400
gaatgcgtac tctgcgccgc agggctgtgt ggtggactat acgtctactc agacaatcag    14460
ctacaccaac aagtcagggc tcgcagccac agcagcaatc gacgaacctg ggttcagtaa    14520
atatggactc caaattcgtg cagcagcagg gcaaatcctg aacccgtcca acatgcctac    14580
tggtatggta gggacagtgt tcgcaatcgt agatgatgtg cctactgttg gtattggtat    14640
gctggataaa agcaacttgc tggaatactt cagccttgca ctgtctatca gggatctcaa    14700
ggtatgggca tttgctttaa caccatatca aatctcagca cttggagtgt aacagatggc    14760
aacaagacct acacttgcgc gaatttgggc gcttagcggg gcacgaaaag accctgggag    14820
tctgaaatac agtaccggct ggattgggga aataccgacc tttgaggtac tgaacttcca    14880
gatgaaccgg attgacactg cgctgctggc cttcgccgag cgtggtgtac ctgaatgggg    14940
cccggacatc gagtacgtac taggtgctca agcatttgcg tccgacggca agatctacgt    15000
gtctaaggtg gcggcgccta gcagggcact gtcaccgcag aacaacctga ctgagtggga    15060
```

```
ggaatcctca gcgcagttca ccatggcaca acacgcggcc atggtagcca agttcgatgc   15120
gcacatcgct cgaatggaca accctcatgg ggttactgct gctcaggctg gtacgtacac   15180
ccaggcccag atcaacgaca agatcgcggt ggtaaaccag aagatcacct cgcacacgtc   15240
agacatgggc aacccacacg gcactactgc gtcacagatt ggcgctgtac cgatcactgg   15300
tggcacatac actgggcccg tggtctttgc gaatgcggag accaagatca acccaggtgc   15360
aggtgaccat gctgtatttg ccgacgcaac tgccgtggga ctcaggtaca acacgatcaa   15420
gatcggtatc gagaagagct ctggtcgggc attcatgcag aacggcgcaa gtaagcaata   15480
cctgctgaac gagccagagt acgttgagct gcggaagacg gtagagaaga actacgcagt   15540
gccgactcca gacctggaac tggacttgct gagtgacatt cacatcaagc aaggaatggg   15600
tttctcggac tttgtgcgtg actccagtcg gacttacacg gacaaatctg gcatactgcg   15660
gacagcagct gccggaatgc caaggcatga acagcaaggt ctgctcatcg aagccaacta   15720
tcgtgagtac ctgtcgattg acgcgccgaa taacttcgcg ggcttcgtag attctacgat   15780
gctgattgaa gggatcatcc gggaattccc gccaggtatc tcaaccatcc tgcagaccga   15840
cagttcaggg cgagacgact tcgtatacgt gtcttccgct ggagtggcaa ctttccgtat   15900
tactgactct ggtggtcaag tgcggaactt tgttatcggc aatatccaag ctggtaaact   15960
gttccgtatt gtggtagtcc tgaccgccac acgatacgcc acgtacctcg atggggtagc   16020
gggtgcagct ggggcaatct cgttcgcacc gacactggag tacagctctg tgcgagtagg   16080
cgggacggca atcaaccccca cagcctggtg gtgccgcaag ttctcggtat gggcacgtgc   16140
tctgacgccg gaacaaatca cgactctttta aggagcttaa atgaagggat attccttcag   16200
cgagttggta aagctcgcag aatcgatggt gccgcttaac ggcgggacca tgacaggtaa   16260
cctgacggct ccgaagttct tcatgtctgc tgcacaggat atggcagcta atgctgctgt   16320
acggaaggac tacctggagt cggtgcttga tggctcaggc tacaagaccg taacgatcac   16380
agccacgcat actgtgacac ctggccaata catcccgatt actatccgaa gtctcggagc   16440
tcagggtggt gagatcggga tttcgacggc tactggtggt agcgccagtc cgatgaactg   16500
caacacgttc gttggtaaag tgttcgctgg tggctggtca gaacaaggct cgtgggtgtc   16560
tggaatcttc aacatctact cagtgtctga gcgagccatc gctggcttct ccgctggtgc   16620
tgagatctca ggtgccttcg cggcgtacat cgagtctcag gcgttccctg tgaagattcg   16680
tgtacctcgc gacgcagtgg tcgattacaa cggaggtgct gttactatcg gcacatctac   16740
cttccccgta cgtacagggc cgaactacgt agcaggtacc aagacagttg agctgattga   16800
cttcaacaaa ggatctgggt attacgatag ccagccgtat ctgggccgta gcgtgaacgc   16860
cttgtacggc aacttcgatg atttgaagat cactgctgca cagggtactg ctgctgaatc   16920
tgctgtacgt agagactacc ttctatcctc gttgagcacc aagttcgaca agacaggcgg   16980
gactatcacc ggaagtgtag tatcgcaagg cagcatcgaa gccgcgagct acatgcagat   17040
ccggggtgcc tctaacccga tgttggaaat gcaccagcca ggtaactcag caatcctgat   17100
ctacaagcag accaacacaa cgaacatcag attcggacaa ggtaacgggg cgggggggcga   17160
ggcaaaaggg tatgcgtcgc tcggtaactc aggttttgaa ttgctagtgg ggaacctgaa   17220
gacctactat aacaacgatc ggggatggac cgacattggc acagcgatgc tgtacggtaa   17280
cgaggtgcaa gtaagcgaag gatcgctgcg aggcttcctg agtcaacggc agacgttctc   17340
tggctaccac tcgattgagt acggttatgg agcactctcc tctgcgaacc cagaatctgg   17400
ggccaatgtg ttctgggcca ctgacggtgg tacatggaca aggcaatggt tcttgtacaa   17460
```

```
taatgggatg ttgcggccgc ctacttcagc tggatggtat atcaacccga acggtgactt   17520
atactcacca agacttggca ccacggttgt ggactgggcc gccgccaacc tgtcggctgt   17580
aaaccatacc cacctggcgc agattgcgaa ctacaacatc gtgcaagggc agcacagcgt   17640
gatcgggtcg tacatctttg cagcgttgaa cccagcccag aacgcgtcgt cctgcaaccc   17700
aggcagcaca gtggcaggcg cccacctgta ccctgcagct tgcgcggaat ggagtcagaa   17760
cagagcttgg aacttccaag gctcctggat gtgtatgggt tttgtagacc cgaacaccga   17820
taaccgttgg gatgaccgtg ccaccctgtg gttccgagtt gcttaaggag caataatgca   17880
agaggaagaa gaaaaggtag aattgcctgt aggtgaagct atccacaaac acgaagggca   17940
gcagatctgc gtgctggaag tgaaagacct ggagtgggct aaccacgaac actcctcggt   18000
caatctcctg gtgcgcttca gccactggcc ggagcacttc ctgccgtaca cgctgaacaa   18060
gtacgactcc actgagcacg gccaagaact ctacgcagca tttattgctg gtaagcttgg   18120
cgagcctgct aagtgcactg caccgacccc ggagcagcaa gctgagatga tgttcccagc   18180
ctacaagaag tcgcagcaag acaagctgga gcgtagaatc gcgccgctgg ctcgggctgt   18240
agctattggt attgccactg aagaagagac cgagcagctc aaagagctcg aaatcaaatc   18300
cgtgaagatg atgcgtgcag tcagtatgca ggacgaagta ttccagtgag gtagtaatgg   18360
aagaacttaa gttcagccag atgcagcttg cagacccact tgcgggtagc gagatggtgc   18420
caattctgca agcggcgtc aacaagctta ttccagcaga ggtcctgaaa ggtcagaacg   18480
gcaaggacgg tgcagatggc aaggatggca ccaacggcat cgacggcaga acggtgttg   18540 atggtaccaa cggtactaac ggagttgacg gtgatcaagg ccctccgggg cctcctggaa   18600
cacccgcgcc gatcgtagat gactattacc tggacattta cgattgggct ggcgaccagg   18660
ctatcgctga cggcgcattc ctgaactttg ccagcctgcc actggtgaag aaagcgggca   18720
gcactgccgg aactactatt gccgccaatg cagtaaagtt ccctaccaag aacaaaccgt   18780
catccgtagt gtttgtgctg cgaattaccg gcaccatcgg tggctctacc tcccaagcaa   18840
gggaatggcg tatccaaatg cgccgtcctg acgggacagt tgttggttct gtcgccgact   18900
taaagatcac cggcacaact attgtcaatc gtgatgtcac tatcactagc cacacttggg   18960
acgcgaacga cccgttctcg gtgacaggta tccagctggg cttgcacaac gtgtcaaccc   19020
aggcgatgac tatcacggcg ctcagtatcc gtgtgcatcg caacgtcaat ccggagtgat   19080
catgacaatt actgaatgga tggagaactt tgcagctgcc gtagcatctc gacagtacaa   19140
catctacaac acccagacca tcaaggcact gaaacaagct gccgatagcc tgtctgctga   19200
agaatttgtc gtcaaggcaa agcagctgtt cctcccgtac gagcaaagta acatcacctg   19260
ctcgtccctc accggccact accacccgca ctccgcgaga gcactgtggt tgactctgga   19320
caccatcgaa atccctgtag cagggcgtat ggtctccgaa gacggtgcgc cgctgataag   19380
cgaagatgag aagcaactgg tagcagaagg caacacacct taggataacc tatgactacc   19440
ccagttgctg tcggagaagt tgttgcacgg agtgccacct tagagaaggg cggtctcttt   19500
gtagtacttc tcgtagtcct gtatatgggc tacaacatct ttcaaaccac cagtgagtct   19560
gacaagaacg agcaaaagct tattctcact caactcacta ccatcgccca acagcagatc   19620
actatgcagc agtccctgac taacactcag gcgtccgtcc aggctagcca ggatgcaacc   19680
cgtgatgtac tgcgcaagat ggaacaaatc gaaagcacca tgcttcgcta cgtttattac   19740
aacgacgcga acggcacctt ggtcatacga actccagatg ctgttggtgg ttctgaaatc   19800
```

```
aagctgaaaa ccgaaccgaa aggagcacga taatgccgct gctgaaagca atcctctggc    19860
cgatcctcaa aaccgtcggc accaaccttc tcatcaacct gatgtctgag ggcatcaagg    19920
agctcgagaa gcgccccaac tcctctgcta ccaaagaaga cgtcaaagtc gtcgaaggta    19980
tcaagaagct ggtgaagtga tatgagccag tctcgccctc acttcaaaga gtctgagtgg    20040
aactgcaagt gtaccacctg taacaaggcg gtgccgcaca agatggacca ggcagtaatg    20100
gataaggtgg agcagctccg agtcctggct ggtcgtcctc tgagcctgtc ctccgcgtat    20160
cgctgcgcca agcacccttc cgaagcaaag aaggcaactc ctggtcagca taacaagggt    20220
ttggcagttg acgtggccgt cgctgacggt gctcaacgca tgcagatcat caagctcggt    20280
ctcgaactcg gtgccaccgg tattggcgta gcaaactcgt tgtgcacct tgactggcgg     20340 aaatccacac ctgtcgtttg gacttattcc taagtctttt cgatagaaat tgtaacaaaa    20400
tgacccagaa atgggtcgtt ttctaaggaa atcaatgcaa aagtacatga aactcctggg    20460
aatcttgatg cttttgcata tatttcctca gaaagcgatg gcttcgaaag gccatcatta    20520
tgacaacact cggtgttacg cccaggcggc ctaccacgaa gcccgttcca ttgacagaac    20580
ggccatgagg cttgtccaga gcgttgtata caacagagtg aagatgaagg atacccctag    20640
ggatgcctgt ggcgtggtat ggcagagagc ccaattctcg tggactctgc gccatccgca    20700
ctcaatcggt gccctgccga cagccctacc gcccgctgac ggggcggctc tcaaagaggc    20760
actctccctg gcccgctctc tgcgcgccgg tgactggcgt ccctccataa cggcagacca    20820
tttcttgtcg ccagacgcgc tctctggggc caagacgggc aggccgcgat tcccagcgtg    20880
ggcgcggtgc ccagcggggc agcctgaccg ctgtatgtca taccagggggc taaagctcct   20940 agcgccggac ttcacatatc gtggtatctg gttttatact atcaactaag agataacgca    21000
aatgaaagaa caagtagtct acatcgtgat gtatgaagat aatggccaga agtatgttgg    21060
caatccgtac ctcaatccta tcgatgcaaa tgaagaagca gaagagcgcc gccaagtact    21120
gaagaatgca ggagcatctt gggtagtaca gcgcaagatg cggagtcaag aatgcagtta    21180
ggatcggtcg acctcgtcag agggagatag atagccttat taagattcta ttattgagta    21240
accaatgaga ttcttaataa gttagttaat aagattcttc gtgagtcact aatgcgaaga    21300
atgcgaagaa gaattccagt cgaccttggt ggagtaactt agtggcacag acgtagattc    21360
cttatgagaa aaaattttg gacccatggt acctttatgg aaattatgac gaaaaatt       21420 tttggccaag aatagggtgg gggaaggatg ttgttgaatc ttgacttgat gggacccgtt    21480
cccgacttga ttccaacgta cttctatcat actcaataag gaatactact atgtctatca    21540
tcaccatgaa caacactgct gctgccacct tcactgacac catggttgaa gagcttgaga    21600
tggttctcat ctccatgctt gactctggta ctatcactga agagcaagct atgaccctca    21660
atgagtgtcg tgatcttcgt tcactgcgta tcaatgctct gaacatgggt cttggtgaag    21720
agattgtcca tgttgttaag gtaatcactg gtgagtatgt caaccagcct ttggttgatg    21780
gtgctaatgt tgatatcagt gagttcttta agtgtaatac ccctgaggag gctaaagcac    21840
tccaatcttg ggctagtgtg tttgatgttg ttatccctac taccatgtca gttgtcgagg    21900
agaaacctat gaagaccgcc aaagacgtaa gccgtgagtt caaagccatc gtggaagctc    21960
gtgatgccat cgaatccagt cagattcgct tggatgacat tgagctcaag agtgccggct    22020
ctatcgctac tgctctcgtt catgcattgg agaaggatgg gttctatacc cagtacttgc    22080
cgctggatga gaatggtcag cagactgata gtcactatca ctttgaggcc aaggcaccga    22140
acttcgacaa tcgttctgtt gctctgcttg ctgtccagct cgctggtgtt ctgccgtaca    22200
```

```
ttgacgaaga atacgacttc gaccatgttg tgcaaacagc tgtgttccgt cgtcgcttcc   22260
gtgacattgc tcgtgctaac actttcatcc ctggcgctta ccacaatatg atggatgctg   22320
ctggtactac tcactggcat gagaagctgt ccaagggttt ggagctagct atcaaggctg   22380
gtctgctgga gagcgttgc gaagatggta tcacctacat caagcacact aagaagtaca   22440
ttggttcttg catctctcgc actagcgtga tgcatcagtc tgaagccatc accactgaaa   22500
ctcgtcgcaa agagcgtgtc aaaggtcgct ctaatgctcg caaggatggc acttctaagg   22560
aagttcgtga ggcactggaa ttcatcgagt cccaagctca atgtgttaac cgttggttgc   22620
tggatgcaat caatggcctg attggttact gcactactaa caatctggct gtgccttctg   22680
tgttcaatga atctcgtcat gtgattcatg ctccaacga gctggctaat gttgctgagt   22740
tgttctctga gtacttccat gaccttcgtg gtcgtatgta ccagtttgct cactgtggtc   22800
ctaacccgca agcatctgat atggctaagg cattgtgcta ccacactgtt gttaaccctg   22860
ttgctaaggg tagtgagcag tatcacatgt tcctgaacga aatgttcggt gaagtgatcg   22920
gtgatgctga tagtgtgtgg gccactgagg cttacattcg tcgtactgct gaagagcctg   22980
tcaaagctct ggtacatgca ttcaatacca acaatggtga gcttccgttc aagaagttct   23040
tctcctacat ggacatgtgc cgtacttggg tgagcttcga agacactggt atgggcgaga   23100
gccgtcttgg cttTggtcct gatgctaagt gctctggtgc tcaaatcttc tcaatccttg   23160
ctggttgtaa gaccatggca gaagcatgtg gcctcatcac tggctatgag cagaagcctg   23220
ctgacccgta caacatgtca gctcaggaag ttaacaacat cactcgtact atgattgacg   23280
ctggtcttat cccgactcgc acaatcactc gtaatgagat taagactccg ttcatggcca   23340
tccaatatgg tggtggtgtt ccgtcactgc gcttcaagaa gttcgagcct actatggaag   23400
ctcttggtat cgccagtgat cgtcgtaatg agttctgcca agatgttgtt atcgagggta   23460
tcaacaatgc aatgggtcca gtcattggct cgttcattga agttcttcgt aagtctgctg   23520
aggcctactg cgaagagcac aatgttgatt acttcgagca tcgtcacatt gatggcttcc   23580
tgtgcaccaa gaagggtgaa gctcaagtcc gtatgacttc tgagccgttc atcatcaact   23640
atggtgctga tggtaagggt gttatctttg gtagcaaaga gaaggctact ggttggttgg   23700
tagagtctcg tacttctggc atcctccagc gtcgtaactt ctgctactac ttcccggtac   23760
acttcatcca aggcctggat gctgtgatgg cacgtaagat tgctcttggt gctaagaaag   23820
ctggtcttcg tggttactcc actatccatg accagttccg tgtatgtctg gaagatgctc   23880
ctcgtcttcg tagtgaggtt gttcctcagg tatacgttga catgttcatc aacaatgacc   23940
ctgtaactca tctggccaac cagatgggca ttgagatgaa gtggggtaac ccgctcaagc   24000
aacgtgtgca ggtgctgact gaagaaatcc tgttcagcaa ggatgcctat acttcgaat   24060 aatcgaacaa gggaatagtc tgttggtaac tcgaagccat tagcaatagt ggcttctatg   24120
gtactagcag cgctcgctta gagccactct taccattgat atgaagtagt gcccaccgtt   24180
gccacagcaa ccacacctct agatgcttcg ccacgggagc ctctcaaaga aagaccagg   24240 ctctagcgag ccacaagacg ctagcaatcg gctctacgag ccaaaagctt ctgacgatag   24300
ctctgtcgag ccacaagtca ctagcgacct tccattgata tcctcagcgt atagttggtg   24360
gatgcaaggg ttattgctat agtctattgc caatataata actaaccacc ataaccatgg   24420
ttacggccct ggcgggccaa agaagatgag ggcattggta ggctaaccga tgtatacgca   24480
caggcccaac cacccaacga agcagcaacc gtgtaggttc acttctacgg gttagtaagt   24540
```

```
cacggcgtct cctcatcgaa actagggcat cgtacccgtg taatgaagac aatgaagact   24600
tgtatgatgt gctgttccac ctacggaaca atcaccgtgg aacgtgagat actaccgtag   24660
agcacatatt tctcctgatt cttattaagg ccgtgtcggc ccaagggtca cgataaatat   24720
tatcatcatt tcaagaatcc ttgcatagca atactacttg tatagatggt atgactgtgt   24780
agagaagaat aatcgtatga gacgtagtat gagacgtccg tatgatgtgc gagtcgaaga   24840
ctcttagtaa gtacacccac agtatgagac gtaagtgggg tgtgtgtggg gacgtggaag   24900
gcaagcggaa ctcgagcgcc acaagacacc agcccctacg tcattcacag acacaggtat   24960
gatacatgta tgacctacat aggtatggtt attacgttac ttactaagag cctacggctc   25020
ccatagggct cttcgagccg aaagtctgtg ataggcatat ggctctacga gccttttgta   25080
attgatgatg ataatattat tatcattacg tatgtctatt attaattatc atgatgctaa   25140
tgtcgcttgc gatttgtagc ctaacctagc ccacaggagg aaccatggca aggtgctaa    25200 actacgctcg agtacgtcgc atccctgagg gtgcggtata cattggtcgt ggaatgaagg   25260
atatcccaga gaatcctttg ttcaagaacc cgttcaagat gcacaacgag tcacaacgcg   25320
acttggtgtg tgaacagtac aagcaacacc tatggaagca aatacaagct ggcgttgtaa   25380
ccaaagagca cctcatggct cttgatggca aagacttagt gtgctggtgc gctccaaaag   25440
catgccatgg tgacactatc ctgaaggcca tcgagtgggc caaggtgaac atgtgagaac   25500
atcatacagt caccacgtgt acaagaacgg ctcatcgatg gtgaagtcga tatgtcacgt   25560
caccatgcaa ctgacaacgt cgttcaacag gcaagagcgc aggtggaact acaagtgggt   25620
aagaatgcga actgctaaag ttgttcgttg tgcaaagaca ggcgtagtat tatggagtta   25680
ctccgttaac cacgctatgg gaattagtat tgacgatatg ggagaatccg atgccagcta   25740
aaataagtcg tgcagacata ctgagagaca tccgtggtat ctctccagca aagctgggca   25800
agttgcgggt aatcgtggag gagcaataca cgcctcggga ctggttggcg caacgttacc   25860
aagtatccct ggtagtatac cgagggcaaa acaagaatat aattgcccgt gaaagtgatc   25920
tggtaagtcc cgcgcatgtc atccaaggct ggatgttggc ttgtggactc accgccgatg   25980
atgttgaact gaatatcccc aagtaagcaa taggaggctt tatgcccaag ttcatgagta   26040
tcaaagacat gcaacgcctt gtgaaaccag cgaagtacta ctactcgttg acaccacaag   26100
gtcgtgcgaa aatccacgct cagcgtatcg agaacgctat gatggtgcga ggtgactaac   26160
atgtgttggt tatcatttgg ttgtttggtg ttattggtag ttattattta cctttgtggt   26220
gatgataatc tctccgataa caattatcct gagagccctt gggataaata aggctcttcg   26280
agccgcaaga gtatgctcca caccgtcatt gcagtatcgg gtaccggcta tcaagccttg   26340
actgatgcgt gagtctcttc gggtggagca cccattcctt tatggagtta acaatgaaat   26400
atttacttgg tctggtaata gtactctttg cgattgcgtt agtctcggtt atattgatga   26460
ccgtggcaat tgccttcggg taccaaggca tatcgggcga acaatgggct gcggctgcaa   26520
tcctcacgtt catcctttgg atcaccgaaa acatcgtagc gagtgtatgc taatggctaa   26580
atttattgca cctgagaaag gcggcttcct gtcctactac gggctgtcga agtaccaact   26640
caactccatc ctgcgtacca atggctacgt gcaggacatg cgattctact ccgacgagga   26700
taactcgttc gtgctggagc gtgcgggtaa tcccaagaca ttcgcaagac tgttctggac   26760
cagcgtaagc ggctggacac tgcacgtcaa gctggaagac gacccgctgt ggatcgtccg   26820
tagcgaatag ctaactaggt gccattcatt gagtggcatc tgtggtagtt atttctgact   26880
atcattttat tggagaactt tatgtacacc aacgaaatgc ttgaacaagt tttaacggca   26940
```

```
atgctagact ctggttcaat ccatgaggac acctgccacg ctctgctcgc tactaacacc    27000
aagatgattc cccgtcttgg caagtttgtt gagcaaggca ctctgtcaat caagactgcc    27060
aattccatca tggctggtct gcgtcagctg agggccaaca gatgagtagc cacctagttg    27120
atgtggacta ctcgcaaatc gaaagccgtc tactggcctc caatcctgag tggttcaaag    27180
accagtattt cgcgcattac agagatgatg cgaagtactc ggttaaactg cgttacgaca    27240
tgactccagc agcagatact catatcgttg actggggcca cctcatgcgc atggttcaac    27300
cgattacagc aactggcgtc aacgagcttg caagcttgaa ggccaaccag attgctcaca    27360
ccaatcagta cacgattgtg agggtccaat gacaatgata ttccgagtcg caatagtcgg    27420
cggccgtgac ttcactgaca tgactaaact gactgcatgc tgtgaccaca tgctgagcaa    27480
taaggtaaac ttaggctacc gaatagtcat aatcaatggt actgccaaag gtgctgatga    27540
actcggaggc cgatacgccg acttgcggaa ctacactcaa gagaagttta cctgagtg    27600 ggaaaagctg ggcaagcgtg ctggcatggt aaggaacact gacatggcca accgtgcgga    27660
tgctatcata gcattctggg atggcgtgtc aaagggcact cgaaacatga tccagacctg    27720
ccaaaggctg ggtaaaccga ttcaagttta caaatactaa ggagccaaga atggctattg    27780
aagttgtaga atacgtacgt cgtgtcatcc tgcgtaacaa ggtgcgtcaa ttcaccctga    27840
accagctggc agacaatttt aagtgtggtc agttgaaggc caaggtcatc tactacgcgg    27900
tagtgactgg ctgcaactct ggcaccatta ccaagctgac catcagcaac gatgactacg    27960
ctcgtctgtg ggcgagggac cgcgacatcc tcaacgtgat caaggagctg taatcatgcg    28020
cgacctgaca tcctgggaag taatcacagt tgtgatctcc gcattcgctt tgctggtgtg    28080
gctctggttc gacctcaaga agttcctgct caagccacgg gaaattccgc agtacatgga    28140
agccaccctc ggcttctctg acgcgttcgt tccgtccaag cacaccgtgt ttgccatcct    28200 tgactgggaga catggtgtgg tctcgatgtc attgaagttc gccggcctcg gcagcgccca    28260
cgacatggag atggctagct gtcatgaaca caatttcggt tacactcatc tcgcagaaca    28320
attcgtgagc aacgcgatta tgtgcagcat gagtgtagat ggtatcaatg aacagcaagc    28380
cctcgctgag gtgcgtagct ggaacatcgt agtaagctgt actggtcggg cgcacaatgt    28440
attcccgagc atcaacgccc agcatcctgc ggcactcatg caagatgcac tgcggcatgt    28500
tcgcaatggt tggagtcaat ccaatgcgag tcgtaatttt aatactgctg gctagcctgt    28560
cagcatgcca tcctatattg gccaacatgg acaaggtgta ttgcaccaag agtgcacttg    28620
ctgaactcca agaaggccac aagcggatcg ctgccggtaa aggtggcgat cttggtaaga    28680
aaatcgctaa agacgcgttc gaccgttaca tcgaagagaa gtggttgaac tgcaaaattc    28740
aggagaatca gaatgatcag tcaagagaaa ctcgccaagc tcactaacac tgctgagctg    28800
gccaagaaag tttgtgcaat cgtcaacaca ctggccgtgg gcgaagcctg ggtggccggt    28860
ggtatcgtgc gtgacctgtg ggccgcgcag accaaaggtg ttgacctcga aggcagcggc    28920
gacatcgacg tcctgctgat caactgcccc aacgacgacc tgaaccagct gggtgctttc    28980
atctctgctg ctctggacat caagggcatc aaggcgtact gctcccgtgt ggactatagc    29040
tacgaagcca cagaagatta tccggatgca gatgaccgtc tgtacggcgt gatgcagttc    29100
agcatctaca gcagcggggc agcggatgca agcaagatcg aaatggacat cctggtgtac    29160
gaagaccgtt tcgagacgtt ggaagacgtc atggacacct tcaactgcaa catcaacaag    29220
ttctggttcg atgaagaagg caacggcaac accaccttct ctccggagca gcccttccag    29280
```

```
taccgcgaag gtgaccgtga gaagaacgaa gaacgctacg agaagtgcgt gatgcgttac    29340
aacatggtgg ccaaggcagc tcacccgtac cagcgtatcg atgagcacga gggcatgacc    29400
gccgagcaag tcgacagcca attgccctgc tgaggtgtaa catgattgta cctcaaaaag    29460
ggtatgtgta cagcatctac cacagtcgtc gtggctggga gaagctgacc gtctgtgaga    29520
cgtctggaaa cactgtgaag atggtgttcg aggaagggtc gatgaaaggg actgtgcggc    29580
ggatgagcat cggctgctgg aatgaccttg tcaagggcaa tcgcctccaa gagggttgga    29640
ccagcaccac gccgactgtt gaccagaagc tggcggaaat cctgccggta gaagtccaca    29700
tcgaacattc ccatgaaaga ctggaagcaa tcgctggcat accgggcgca atccgccatg    29760
ctggtgagac ccgtgatgaa ttcctgagcc gccttgagcg aacacttaaa cctaaggaga    29820
aacccttgaa acttcgtatc gtagatatct actgttttga caccaccacc aaggacctcg    29880
acgctgccaa tcgcgtgatc gacaaaatcg aaggccacgt gaccgacaag agcgacaacg    29940
acactgttgt tgacctgctg gctgccggaa agttcgtagg cgccctgagc gcccacaacg    30000
agagagcggt tgacgaagag tcgaagcacc tcaagttctc cgacatggaa atccgtgtcg    30060
tagagcgtgc tgcggtgtaa ggctcttcga gccaaaagtt agtgctaaag tcgaagccat    30120
tcaagtagtg gcttctatcg ttatcactac aacaaaggag tgagaatgac cactagagat    30180
tttgatttca ccagtggaat gccgcccggt actaacttgc gtgtgaagtg ccagtcacc    30240
gctgcacaag taagaaccac cggtacgctc tgccattttc gttctccgca agggcacgaa    30300
ttcatgcgca tggttatcgc tagcgccggc caatacctca cgtgggtaga cggtctggag    30360
cctgaatggg ccatgccgta tgcaggtgac gacatgtggg cgactttcaa tgacgggttc    30420
ccccgtcgag tgtgacacag cctaaggaga atccaatggc gaaagattac ctttgcggtg    30480
tagcagcagg tgttgattta gccgtcaacc gtgctgtgcg ccgtgcagta acccacgaga    30540
agggcatcaa gttcatcttc cgtgactcga tgaccggcca agatcgtgag aaactcattc    30600
ccgtaactgt ggatgaatac tgcgactgga ttaatggtag cctgattcag gacgccatgc    30660
cgcatatcca ccctgatgac cgtgagttgt ttctcactgg gatggtgtgg taatgaatac    30720
ctggttcgta ctgttcatca cactgaccta cggcggcagc catgagttcc gtactccgta    30780
tcaagactac cgctcctgcg aagaggcggg ccaacaagtc tacaacatgc ggtacgtcaa    30840
ggacttcatc tgtttgccag taaagcgcta acgcgccaaa agagagtgac taagtaactc    30900
atcaactacc tgctaaggag gatgatatgt agtcactcat gttcaatcaa agggccttcg    30960
gcccacaaga aattcctgga gcaagtatgc aagctatgtc tacccaggcg agcagcatgc    31020
ctgctccgcc gattttcgcc gtcatcccgc gtgtaccttaa tgacgaggta tgcccgtgct    31080
gtggcactgt tgtgcatcat ggttactgtg gtgcatgtga taaaccatt gaaggataag    31140
gacatgcatg gtgtcaatgt ctctcgcgtt ttgggctccg gtgcaattga ttttgctact    31200
gaccctctgc gtattggtgt ttgtaaaggc tccccaatgg gccgcctcat tcaccgcagt    31260
aattcccgca aaaccgtggt gcgacgtgtt cagtcgtctc ccgctcatgc gtacaactac    31320
accatcatgg gctaacccaa caggcctctg cgagcaaatc cggattcgga aacagacgtg    31380
gaaaagttga agttagccg atggtgtagg cactacaacg ggctccggaa cactaccgga    31440
gtcctacaat tagtactctt gcgctggacg cttggagata acgctgaaag aaccaaatgc    31500
gatttggtag aataggtata atgccaagta tgataaagcg tgagagtcct aattatactg    31560
agtgggttaa aggatggcac ttgtagacag ttcgtctaga gcccaggac aggcgctgcg    31620
cgatgcgtca aacacaggtt caactcctgt actcctatga gtgtcattgc tttaaccctc    31680
```

```
ccatcaacgc aacaaagaga atcactctat gcgtaaagaa gacaaagtag tatccctgtc   31740
caccgctact cgtgccgagc gtaagcatgc caagcacgta gcgcgtaccg aagcccgtcg   31800
tgttgccaag tgcaagccga actggcagaa ggagtggaag aaccacatgc tgcaacagcg   31860
cggcatgaac aagatcatgt ccctgatcgg tcgcggcatc gccgtacaga aggtcaagaa   31920
cgctaaggca ggtgtgtaat gagcaacgtc atcaactacg aactcgttcg cgccggtaag   31980
gtgatcttct cctccacccg taagctggac accatctatg ctcaccagaa gcaccgccgc   32040
agcgctggtg tgagctaccg tgaaaccaag gccaagtaag gtatacatat gccctattta   32100
ccgattcatc ctcgtcgtgc gctccgtgtg ggcgacgagg taattcacgt tggtgaaggc   32160
gtgacctacc ggggtcgatt gggccgcgtg gtatcagtat caggtagcaa ggccagtggc   32220
caagtgaaga tactctggga ccacaagatg caggcgctgg actacagcat aggctggtgt   32280
atcaggatgc ttggcgtgca cgtgaactgc ctgcgagtca attaccaaga cttccatggc   32340
aagacttacg tggacaagta tctgcactgg gcgttccaga agggcgacgt caccaaaggc   32400
ttcttcctga ctccgcatca cacgatgaag gccaaggaag acgcgaagct gcgtgccgaa   32460
gaacagtgcc gcgtccagtg ctgcaaagtt gacgtcacga gcgactacca gcgtggtctg   32520
atggcccaac tgaagcgcga ttggtccatc ctccagcatc ctggcctgta caagctcatc   32580
ccgactaccg atggtctcgg gtatcgagta gaggccatcc ctgccaagcc ggcacaacct   32640
gtacaggaga agcctgtgtc caacgtagta taccctgtga ttgccgagag ccgcgagaac   32700
ggtcaaatca ttcacattgc atccgagaaa gagctccaga agctcggtgt cggtagctat   32760
acgctgtact cgaagtcctg caacatcgca gttgctccgg tacagcagaa ggaaatcact   32820
ttcctgtaag cataactcga gagtcctgac cgcctttgaa cagggctctc tatggtatgt   32880
ttaccagata gttttcgtca gtaacacgcg tctgttttta tcatcaaata aatgcaaacg   32940
atgatctgat gttggctgcc gcctgataag cgaaacgcca cgaggtattc tagttcctcg   33000
ccaagcaatc tagcggagtt cctcactctg attaatacag agggcataac tcgagtgtcc   33060
tgcacgaata cagcagggca ttctctggta tgtaaccaat tcggcacttc gtgccacaag   33120
gagttgatca tgtcttacga tcgtcgtaac gaccccaacg atggaatagt gtctgccgag   33180
atgtctctgt gggacttcct cggaggacta ctcctttcat gcgtactagt attccttatt   33240
gtagggtact gcgcaaaata aactgtgtat gtcaacttgg agaaaccact atgacaacca   33300
acctgcaaac cccgaccctc cagcaccccg acctggctcc gcaacaaccg cagaccagtc   33360
agtaccctgc tgagatcgcc aatttcactc tgctcgctgc ccgtaaccgt accagtgaac   33420
gctcaccgca ctacttcgga tccttcaaga tccagggtgt ctggtaccag gtctccacct   33480
ggattgtgtt ctcgcgtagc ggtggcgagc agcaactgtc caacagcatc cgtccgtgca   33540
ctccggaaga agctgccaag catgaagctc gtgaccagca attccaagcc ggtcagcaag   33600
cacgtgctca gcagaccctg gccaggtgc ctaatccgat gcatgctccg gccaacaccg   33660
gcacaccggc tgtggacccc aaccacccctt tctgacaaag gatcctgccg tgaacaagtc   33720
actgcgtaaa ctggcgagcc tcttcggggg ctccaatatc ccccaggctg gccgtaacgg   33780
tcggcttgac atggaccgcc atctgatcaa agagaccatc ttccgccaat gcgatgccca   33840
catcgacttg aagcggatta ctcgtggtac ctttatacac gtggtgaagg caggttttcaa   33900 atcctctgtc gtccgcctgt tcgaccatga gatcgtggtc agcaacaagt acatcaagca   33960
gtcttaagga gaagccgtgt ccaactttac ggatgaccaa gagatagtcc tcgagattat   34020
```

```
caagcagtgg ttacgcaatc aggacgcggc gtttcttgcc cgtgaagaac tcgttgtctt    34080
ctggggaccg attgatggca acttgcgtaa gcaagggtgg aataagctga agctcaacga    34140
ggctgtcagc gtaatccgaa ccacgaaagt ccctgtcggt gtgatgaaac actgcacagc    34200
tgacttgatg cgagcggctg ctcaagaaga aggtcgtgcg tatatcgctg gagtgactgt    34260 tgtaggggc gctgtgagcc cggaatactt caactttcac tctaacaagc ggtctgtatg    34320
cgagaccatc gagcaccgtg ttgccattca tctgatctgt gagcttgaag ccctggacca    34380
gaatgtcatg tggcatcagg tagcatacct gtatgagcag tgcctcaagt acatgaagct    34440
tgaggttccc aactgcatgc agcgtaacaa tttcatccgt tacggcttac aggagtccgc    34500
cttcattgag aagcgtaact ccaagcggta caacggaaga tacgtcatcc gcgagggtgg    34560
caaattgcgg caactgattt gtatcaagct gccgcataag tccggtatca agaagactg    34620 gactaaagac gagatgaggg gcatcgtcct ccgctcggtt caaccgctgt tgaatccccc    34680
tcgtggatca cagtaatcca atggcttcgt agagaagctt ttccacatca agagagatct    34740
ttcatgacta tcaagtccgt acaactgttc gttaccaccg atggcaagca attcgaagac    34800
caggctaccg ccgaagcgca ccaggttttcc ctcgacaacg ctgccgtagt tggcaaagtt    34860
gccacctcct tcgtcaacgt cgccgttgct ccgaacgcca aggttccgg cctgaacggc    34920 cgcacccgtg tgttcaacca gaacgtcgcc agccaggttg tatccttcct gatcgcccaa    34980
ggcgtgatcg ttgctgccga cctggaagcc ttcgaggcca tcgagccgag cgaagagctg    35040
gctgcccgcc tggaagctga ccgcctcgaa gccgagaaga aggctgccga agccaaggcc    35100
aaagctccct ccaaaggtga aaccgctccg gccaccaccg tgaagaaaac caagaagaa    35160 gtcgctgaag acctgttcta attctgatcc ggcgcgctgg catcgcggcc agtagtcatc    35220
gactacaggt aactgccaaa tctagcccct tgctgaaatg acgcgagggg ctatttttc    35280 ccaccgacca tcgagtcatt cagaatgcac tcaatggtga gtgtattccc aatgatacgg    35340
agattccaat ggctaagccc tcgactaagt atccccgtcc tgctgagatc ctgatggctc    35400
tggcggcggc taatatcgac caccggttca tcaccgtacc caatccgcag cacatcgaac    35460
aggagttggc acggctgatt cccgacccgc gtattgctct gcaagtgtct cgcctgatgc    35520
aagagaacca gaacggcttc atccaggcgc tgctgcacac cggcaaccag gccctccaag    35580
ccatgggcta ccaagagacc gacgtcacca aagacgctgg tggtgtagcc ggtcgtgagc    35640
tggttgagca agtaggacgt gctatgcacg ctgctgctga gctgaagaag gctgaagagg    35700
ctgctaaagc gcctgctgcc aaggagtaat catggctggc acttgcgtag agcggatgaa    35760
acatgatgac tcgaagtgca acagcacctc gaagtcgctc cagatattcc tcaacgatga    35820
tgataccttc tcggggttct gtttccactg tcacaagctg gtgcctaacc cctatggtga    35880
caatcctcca gacccgaaag atatccatgt caagacaccg gaagaaatcg cggaagagat    35940
tgctgaggtc aggcagtgca aaacaatgcc tctcaagcat cgcggcatcg acccagaaga    36000
ctggagttac ttcggtgtcc ggctcctcac gagcacaact gacggcacta caccgtatgc    36060
tatcgcgcat ccttatacca agaatgcaaa ggtagtaggc ttcaagatca agctgatcgc    36120
acgcaagacc atgtggaacg tgggtgacgt taaaggcgcc gacctgtatg gttgggaacg    36180
ggcgaagcgt gtaggcggtg gtgtactcta catcaccgag ggtgaagagg atgcaattgc    36240
gctccgcaaa atcctccgca tgacctccac caatagctcc tacgactacc ctgtggtgtc    36300
gttgcctgcc ggtaccaatt ctgtggccat gtgtctggga cgtatgtccg aggaaatcaa    36360
cacacgcttc aagcgtatcg tgctggtgta cgacgacgat gagcccggcc gtaaggctgt    36420
```

```
gcaagaaact cgcaagatct tcccgcatgc tgagtctgct atgctcccag agaaggacgc   36480
caacgagtgt ctgatcaagg ggcgtatcaa ggccgccaag gatgctgtag tgttccagat   36540
ggctaagccg tcacaggcgg ctatccaggt gctcagtgcc gatgacgtca tggacgagat   36600
tatgcaagac ccagagtggg gcttgtctta tccgtgggac gacctgatga agaccacgta   36660
cggccagcgg aagaaagagc tcatctccat cggcggcggt actggttgtg gtaagaccct   36720
gattggccat gagatggctg cgtggaacgc tcgtactcac gggtggcgca ccctgatgat   36780
catgatggaa gagtcaccag cagagacgtt aagaacgtc gcgggtaaga tcgacaatgt   36840
gccgtaccac atccctgtca agatggcga agagccatac gacaaggaaa ggctgcggtc   36900
caccatcgac tacctcaagg cttttcataag cacctgggat atctcgacca ttgaagaccc   36960
cgagaccact tgggctcaaa tcactcaggt catccggact caaggccacc tgtacgactg   37020
tatcatggtg gacaatgcta caacgctgtc ggaaggtctg tcggcatcag agcgtaacga   37080
cttcctgggt aaggtgaaca acgagtttgc caagctcgcg gagaagtttg acttcgaagc   37140
aatcatgttt agccacctga atgcaccgcc gtccaaccaa cgttcccacg agaacggtgg   37200
taaggtaacg gaagcccagt tcactggctc tcgtgcagcg atgcgttact cacacatgat   37260
cttcggcttc gagcggaaca agtctgcgga agacccagac tgctcatact tcgtggtcct   37320
caagaaccgg aagttcggcc gtactggtcg cttcaagacg tactactcac aacgtactgg   37380
tcgcctgcaa cagcgcaact gggacgatga gtcgtaccaa gacaaggcta cggcaagcac   37440
caaagcctcg taaggagaat ccatgctggt agtacctgat gcgtgggaac tgattctcaa   37500
gactcagaaa gacgggtctg agaagactgt taccctgcaa aagtttgtag aagtaactgt   37560
ccctcgcaat agctactccg ctaaagcagt ggacaacctg atggctgttc gtgagcgact   37620
caagaacggc gaagaagtag atggtgccga gatcaacctg aagggagtga ccttccggag   37680
ggcaccatga ccgaccaaga attcttccga cgttctgtgc tgatgttcaa gagcacatac   37740
cctgaaatcg gggacaagac agccattgca cgcgcgcaag agctgactga cgacgtagtc   37800
gaacatgagc agaaaagcgc catggctcgc tacaaggctc cggaaaagta cgagcggatg   37860
ggcaagggca gcatcgtaaa gaaggcctgc gggttctgca tcggcaccgg tgaactgcga   37920
ggtggtagcc aatcgttcgc ctgcccgcat tgcaatggta cggggaaaga gcaatgactc   37980 atccatgta cctgctctcc gagccgaaga acatgttcgc ggcagacatt gaaaccactg   38040
gcctgctgga agacctctat acccaagagg caccgaagct ccataacttt ggtgccaagg   38100
ctatggatgg tactgagttc ctgttctccg aggcctggaa cgtcctgaac acaaaagcct   38160
gcgcggacat ccgaccgctg tcagagctcc aagcattcct ggatactggc ccttgcctca   38220
tcatgcacaa cggtatgtgc tacgatggtg aggcattgat cttcttcggg tacgacatct   38280
ctaaggttcg tattctggat acgctctacc tctcttggta ccttgagccg ctgcgtaatc   38340
gctacggcct tgccgagtac ggggaagaat ttggtatacc gaagccggtc attgacgact   38400
ggcagaacct ctcccaagaa gaatacaacc gacgggtcat gcaagactgt cggattcaac   38460
tccaactgtg gaagcgtctg cgtgctatgc tgtatcgtct ctatgatgat attgaagctg   38520
aggcatggaa ggcgctgaac cacgtgtgtg tgataaaggg ccgccatttg cggaaccaac   38580
agcgcacaaa atggaccgta aatattcctg ctgcaaaaga gctgtccgag cgactgcacg   38640
cagacaagga agaccggttc gtggagctga tcgaggttat gcctcgtaag ccagtgttca   38700
agagcaagaa gcgctgcgcc aaaccatgga agatgaacgg cgcactgtca tctcacggtg   38760
```

```
aaggctggtt gaagttctgt atgctgcacg gcatcgactt caatgacctg accgagttcg   38820
agtaccaaga cggggacgtc gagggcaacc cgaacgctcc acagcaggtc aaggactggc   38880
tgttcagtct cggctgggaa ccgcagacct tcgattacaa gaaggatgat gctggtaacg   38940
agcgagtgat accccaaatc aacgtcaaga atactggcgg ggagatggac ccaggtatcg   39000
agttgcttat cgaggaccat ccagaagttg caagactgaa gggtcttggt atcgttaagc   39060
accgtatcgg cattgttgac ggctggattc gtgacgccat tgatggcaag gtcatggcac   39120
gtgctgctgg cttcactaac actctgcgtc tcaggcacgc tgaggtggtg aacgtcccgt   39180
cagaacgggc accctacggc aaggagctgc gctctctgct gatggcgcct gatgacaacc   39240
atgagctact aggctctgac ttgtcgtcgc tggaagaccg gtgtaagcac cactaccaga   39300
tcccgtacga ccctgagtac gtgaagagcc aacaaactcg tggttacgac cctcacctgc   39360
gtatcgcacg tctgggtggt ctgtgctccg aggatgacga gaagttctac attgactaca   39420
cgcttcgtga agaggatggc ctgccaatta ccgaggaaga caccaagcgg ttcaagccgc   39480
tcaagggtat ccgaggtaag ggtaagccaa tcaactatgg atgccaatac ggccagcggc   39540
cagcaggtat atctcgtgca tctaagatgc cgattgagat ggctgagctg ctgtacaatg   39600
catactggga acttaactgg tccatcaatg cagtggcgga ctccatggag atcaagtcgt   39660
gtaacggtgt gaactggcag cggaaccctg tgtcagggat ctggtaccac ctcaagacca   39720
acaaagaccg gttctcaaca ctgtgccaag gtactggtgc gtacgcattc gacctgtggg   39780
ttgagtctat cttctgcatc tgcgaagaac gctggaagcg tgagcctctg ctgaacggcc   39840
agttccacga tgaactgatc ctgacagtca agaagggcct gcaagacctg tggcgtggtg   39900
tagtccgtga gggtatcacc agagcgaacg gcctgctgaa gatgcgtcgt gaaattgatt   39960
gcgatatcca gtttgatact gtgtacgcgg gaatccactg atgtctcgat tcgaaaagat   40020
ggtcgccggt aacaaggcga tcttcgaata ctgcgaacgt attcgacaaa tgaaccaaca   40080
agaggagaag cctaatggct ttgtttgata aagcaactga gaagtctgct ggtggtaacg   40140
gccagaagat ggaagccccg ctgctggcgc tgggtggcta ccctgccgta ctgatccgta   40200
tcgtcgacct cggcgagcag cccggctccg ctcagtaccc cgacccgtcc tacaagatgg   40260
cgctggtatt cgagtgcctg gacgagttca tggtggacga agaaggcaaa tccctgccgg   40320
acgttccgcg tgagttcgac atggaagtca gctacaacct tgacggctac atgtcgccga   40380
aggccaagct gcacggtgtc atgaccgcgc tggaaggctt cgacaagtcc ctgagcgagt   40440
tgctgggcac tgtctgcacc atcaacctga tccagaaggc caccaaggcc gacgcgacca   40500
agaagtacaa cgccatctcc ggtgttgctg cgatgcgtga gaaggacaag gaacgttacc   40560
ccggcccgtt caagctggag cagtgggtgt tcaacctaga cgccaacacc accaaggaag   40620
acttcgagaa gcagtcctct cgcggtggtc agtacagcca gcagtccaag atcaagggcg   40680
cactgtccct gcacaaagac gctccggcaa ctcgcggccg tctgggtgtg aagctcctta   40740
agatgatcga ccacggtgcc gacaagccgg taggcgaagc cggtgctgcc ttcgacgaag   40800
aagagcagaa caagcagatc gaagctgcta tgggtggcgc agcagtgcct acggaaggcg   40860
ctggtgcgga accgaacccg ttcgattaat cggagacgac atttatggca attccaacaa   40920
tgtcgaaatc cgttgtcgac gagcccgaag acggtcgcta cgactacgaa gagctcctga   40980
tcgacggtga cttgttggtg ttttcctcct gtgcggctgt tgaatacggc cgcactccgg   41040
aagaatacac tctgcaagaa atcctgacca acatcgaagg tcggatcatg gcgatgaagc   41100
gtcgcctcaa ggctcgtaaa gtacgtatct tcttcacggc ggaagacaac ttccgttaca   41160
```

-continued

```
agatcatgaa ggcgtacaag gccaaccgtg aaggcgcgtg gctgccggaa tccttgaaga   41220
atgcaaaggc ccatatcacc accatgttca atggcgagcg tgaaccaggt ctggaagcgg   41280
atgacctcat gggcatctac cagaagattg atggcaccac catcgttgca accatcgaca   41340
aggacatccc gcagattccg ggcatgcact accgctggga gacccagcac aaaggcgagg   41400
ccgtctttga ggtgtctggc tacggtactc tcgtgaaaga atccacaac aagaagacca   41460 agatcagtgg cacgggtgct cggttttct gttaccagct gctcatcggt gatccgactg    41520
acggcgtaat gggttgtggt aagctggaag agtcggtcta caagactggc gcgaaggctg   41580
gcgagagcta caccaagcgt tccggtgtcg gccctgtcgg tgcctacgac ctcctggagc   41640
atgcgatcac gtatcaacgc tgcatggaga tcgtcattgg tcagtacaag cataccttg    41700 gtgacgcttg gaagaacaa cttctcgaga atggccggtg cctgtacatg acccgtaaga    41760
tcaacgacaa aggtcaattc cagctgtggc atttccgtgc cgaagagttg cctaactctt   41820
ggtacgaccc tgctactgct gctgtagtac gtttcgaagg ctagttaata tgagcgcata   41880
cggttactgc aaaagcgaga aagcttatgt cgcttggttg agatctgcac tcagacgagt   41940
gtggtcgaaa cacccagtga agctagagat gctcaagaag aatcgtgtgc gctctgttaa   42000
tccgaagaca agtcgaatgt gctttatgat cacgtgcaag acgtgtggta aagaccatcc   42060
gttgtcggat atcgaagtga accacaagaa tactgtggga actctatcac tggagaactt   42120
tggcatttat tgcgaaagac tcctgctggt agaggagaaa gacctagaac ttctgtgcaa   42180
gacctgccac gaagttgtca cctatcaaga aagatctggg atgacactcg aggaagctgc   42240
gattgagaag agagttattg ctttcttcaa caagtatcca gcaggtgaac agaagagacg   42300
gttcgaattg ggaggcatgg tgcctgccaa gaccgtcgcc gagagaagaa ttcaactgag   42360
ggagtacctt cgtgaacaag ctagaaatgc tggaactggc ggctgagaac gccagataca   42420
acaacgctgg gaagaagtgg cggaagatca gacatccgaa tcaccctgac gaccattaca   42480
caccacatct gatactgcgc atgaagcaga tggatgggtc ctggacaccg ggaatcgtgt   42540
acattaacag cgctggcgaa acattctgcc gtgctgctga caacttcgag aagttctcgg   42600
aggtgtaaga tgcatgagac cattcaaacc atgaacgcat tgcgtagcgg gatggttatg   42660
cgttatcacg cgcagccaga tgtaccgtgc cagtccaacg ccgagcacat gtggggcgtt   42720
gcagtactga tgctgaagtt ctacggcata gaaatgagcg gagaagctct tgcagcagcc   42780
ctcactcatg actgtggtga agccgatgtt ggtgacattc catcaccgac aaagtacaag   42840
attccggaaa tccgtgatct gatcaagcgg ctggaacacg agtctctcaa tgaactcggt   42900
ttcaacttcg aagctgacct ccatcagtca gagaagcaag cccttaagat ctgcgatgtg   42960
ctggaggggt tgcactacac cgcgaagcat taccacctga ctggtggtgc tcagggtggt   43020
caatgcctcc agaactgggt ggacctagcg aagacactgc cgctgacaag gccgcaacgt   43080
gacttcatct acgtgtgcct ggcaggcccg tcacgcagag tagtatcata gtagtgatca   43140
ccgacgtgtt ctaccaaggc gcagatgatg gcatcccagg ccactggtgt gctcagtact   43200
tcaaaggagg ctgggcgcag taccaccgca gcacggacta cgacgagctg aacaatgga   43260 tcaaggagaa cgccaccaat gcggatgcct ggatttaaag tacaccaaga agtgaagaac   43320
acgttgtgga ttgctgcgat tgtggcaggc atagtgttcc actgctgggc aatggcgaac   43380
agcggagtac tactctgctg gttctaccaa gctaaactga gagaattctg atgcaacaaa   43440
gctcactgag tatctccatc cagaaagcac tccatctgca tctggaagaa gagaagaaat   43500
```

```
ccccgaagca cctcggtcac gagtacgcga tcttcgagaa gtacgatggt tggtacatgt   43560
acgttgactg tatcgacggc gtgtggcaag gtatccgctc caagacaggc cgccttctgc   43620
cctccatgca gtggtacaac aacctgctcg aacaaggccc gaagcctaat caagacctgc   43680
gcctgatctt tgaagcagtt atccctggga tgatcttcaa ggacgccaac ggccgcttca   43740
accagaccaa ggagcagctt ggtaacgtag tctgctggtg ccatgatgtg ctgtttaaga   43800
aatacccgca caccatcttc tccaagcgct acgaccgtct catctccgtg ctgaaccacc   43860
tggactatag ctggctgcgc cgtgcgccga ttctggctgt gacccgtgac gttgccgtat   43920
ggcatgagca ctacgagcgt atcatctcca ctccggacgc gtacggccaa aaaggcgaag   43980
gcgttatcgg gaagaagtgg gacgagccgt accacgaagg caagcgtgac tactccttga   44040
tgaagatcaa gtgcgagctc actctggacg ttgaggtgat cgctgtcggc cctggtgcga   44100
aaggctccaa gtacgaaggc agccttggct tcatcgtggt tcgtgagaag agcggccaga   44160
ctcaccaggt atctggtatg tcggatgctg aacgagttga gtggtggaac aatccccagc   44220
tcatcgttcg caaggttgtt gaaatccaag ccatgaagcg cttgccgaac gggtcactcc   44280
gcgaagctcg ttacaaggcc gtccgccacg acaagactct ggcagacatc gattaaggag   44340
aaccgaatgc aaagagtacc tactgtagga gtggccttca acggccctcc tggcattggc   44400
aaagacacgc tggtgaagct catcaacgag gtactgttcg acaagattcc tgtagggacg   44460
cttgccaaca tgatccgtca ggatgcagct gcgtactacg gcatcgagaa cttcttcgag   44520
ctgtcgacgg accgtgagac caaggacacc aagtgcccag gtttcagcat gaccccctagg   44580 cagctgctga ttgattacag tgagaatgtg atcaagaaga atcacggcaa ggatttcttt   44640
gccaagaagt tcgccgagca gatgtctcaa gagcaacagt tcatgatgac cgaccttggc   44700
ttcgttgaag aagctgaagc gctggccgac cgtgtcgacc tgcttatcat cgtgcagctg   44760
gagcatccgg acttcgactt cagccgtgac agccgtgggt acgtgaagct gcatcgcagc   44820
aacgtattca acctgccttt cgtcgtgtct cgtggcgatg cccaatctga cgcccgtcgg   44880
attctcgaag ctatccaaca tgcttatgag gaacgactcg ggttgtaacc aatcaggagt   44940
ccgagttgga ccttagcaaa tacatgaagc ccgttgacat tcgtgtcgta gtaaaaaggg   45000
atggcagcga ggagcctttt gactcctcca aaatcgagcg ttgggcagag tatgcctgca   45060
agcagaaagt gaactggaaa ggcgtagcgg tcaacgtgat ctctcgtctc ccgtccaagg   45120
tcaccacggc tgagattcat cagtcgatga ttgactactg cctggcgcaa gaatctctgc   45180
cgtacagccg tgtggctgct cagctggtat atgctcagct gcgtaagaac atgcgccgcc   45240
acctgagggt tgatgaccgt gacgatatcg gtgacatcgc cttccaactg gcggagctgg   45300
gtctgtggac tcatgagctg tccaatctga tcactgacaa cgaagagctg gtgcagggat   45360
ggtacgacgc catataccct gcgcatctcg agtcctggca agtaatgcaa tgggcggaca   45420
aatatgcgat caagaaagac ggtattccgg ttgaaacacc gcacgtgggc gcgcttggaa   45480
ttgcaattgc aatccatgga gtcacccaag atgcgtttcg actggctcgt gccatcgtgg   45540
aaggtaagat taatctgccc acgcctgtac tcaatggctg tcgtaacgga gactttgact   45600
caatctcgtg ctcggtcatt actggcgcg acaccgttga ctccatcggt gtggcggagc   45660
accttgcgta caagatgact gccaagaagg ctggcatcgg tatcgagatg aacactcgat   45720
ctgccggtga caaggtgaaa ggcgggcgta tcaagcatct gggtaaacac ccgatttacg   45780
ctgccgtcga caagtctgtg aagatgttca cccaagtcag tcgtggtggc tctgcaacca   45840
tgaccttctc ggtgtacgac cctgagatta tgatgctgtt gaagctcaag tcacagcgta   45900
```

```
ctcctttgga tgtccgtctg gataagatgg attactcaat ggcctatgac gataacttcc    45960
tcgaagcggt cgtcaagaac actgacgtcc agaccaagag cgttgacggt ggtctcgggc    46020
cggtctaccc tgctcgggaa atcctcaagg tgttcctgca aatgcgtcag gagactggcc    46080
ggctgtactg cttcaaccac tccgaagcga accgccacac gccgttcctg gacgagattc    46140
gcctgagcaa cctctgccaa gagatctgcc tgccgactgc cccgttcacc gacatgctgg    46200
accttttacaa tccggcactg ggctacaagt ccaatggtga gattgcattc tgctctctgg    46260
ctgccatcaa cgtgtacaag gtctccgaag ctgaatatgc tgacatcgcc tatctggcgg    46320
tgaagaccgt ggacaacctc atcacgctgg cccccgctct gagtgcccca gtggccgaga    46380
aactgcaagc gcggcgttcc ctaggcatcg gcattaccgg cctggcaggc tggctaggcg    46440
agcactctct gcgatacacg gatacggcct cgattgagtc acttgcagaa cgccactact    46500
actggtgcct gagtgcctcc caacgcctcg ttctggaagg cagagcgccc gtctctggca    46560
tccgtgagga ctggctaccc atcgatacgg gccacatgac cgttgcgcct cgcatggact    46620
gggaagcact ccgtggcaga cccagacgga actctgtact ggtagcccac atgccgaccg    46680
agtccagcgc cgtgttcagt gacgcccga acggcctcta ccctgtgcgt gacgccgtca    46740
tagcgaaggc ttcgcggtac gggcttatca agtacatcgc cccagccgct tgcacagaga    46800
gagcgtggga cgtgggcaat gatgtcctag cccgtgcgta tggtgccgtt caggcatata    46860
ccgaccaggg catctctgcc gactactacg tcaccccgag caagtacccg aacgggaaag    46920
tgcccatgtc ggtgatgatc aaggagtggg ttattcaagc caaggctggc gtgaagacca    46980
tgtactattc caacaccaac gacttcaacg gcggtgcgtt ctcccagcaa gaagatggct    47040
gcgagggtgc ctgcaagctg taaggaagaa tcccatgcaa attgaattga cagtggacgg    47100
gaagtccttc aaagtagagc ccatgcaggt agaaacccaa gaggagcgat ttgactcgac    47160
tgtcaagtcg tatctgctgg ctgctgcaca gcaaatcatt cggaagtatc tgttagacca    47220
acaatacccc atccggtaca accaacctga agtacgcaat ctggaaaaca ttgtggactc    47280
agcgttcctg cgcagtggcg ttcacgtcgc ttcgaccatc accagcaacg ataacgggag    47340
aaccatgaat gtcagtcttc aacgccgcta ataccggtta catcaacggc tatccgaaac    47400
tgttcctcgg cgaacagcgt ggcctgctgg acactatcaa tgtccagtac cctgagctgg    47460
aagctcttta ccaacagcag atgtcccaaa tctggaacga gttcgaagtg acctgagcc    47520
aggatcgcat ggacatgcaa actgctgctc cgggtcttat cgacctgatg gtaaagacta    47580
tcagctggca gcacctcgcc gactcggtag ccgcgcattc catttccggt ttgctgatgc    47640
cgcatgccac caactccgag atggagagcc tcatcaacgc ttggtcgttg ttcgagacca    47700
tccacgctcg tacctacagt cacatcgtca agcagacctt cgcggatcct ggcaagatgc    47760
tggaagagac ttacgccaat atggacgtac tgactcgttc caacgtgatt gtagacgcct    47820
tccatcgtct ggaagacgcc ggtgcaaaag cagaagaggc cgatatcatt atcgctctga    47880
ctgcgttgtt cgctctggaa gagattggct tcatggcctc atttgctatc actttcggca    47940
tcgccgagaa tgcgaagaag ttcatgggta tcggccagct ggtgaagctg atttgtcgtg    48000
acgaagtcct gcacactcgg tttggcggtg cgattctcaa gatccaccag aacattccga    48060
gcacctctgc gctcatgcag aagggctggt tccgtgacga gctgaaaggt atcctggatg    48120
ctatcgtcaa ccaggagctg accttcaccg actacctctt ctctgagggt cgtgaatgca    48180
ttggcatcaa tgccgatctg gtgaagcagt acgtactgta tatggccaaa cccatgtaca    48240
```

```
tcgcgtacgg cctgaccttc gactttgatg ctccgaaaga aaatccgctg ccctacatgg    48300
accactggat tgacggtagc aaagtgcagg tagctccgca agagttacag aacggttcct    48360
accaagttgg cgccatcgtt gatgacactg acgatctgga cctggatgat ttgaacctgg    48420
gttaatcgtg gcaaaagaaa atgtcttcga gccagtagaa gagttcgagg acaacttctt    48480
agtcggctgt atgctgcaga actatggcga cctgttaaag gtctccagga cgaagggtgt    48540
gttacgcacc cttccgaatc tgcgggaata cattaaagac aaccagtaca ttcgttacga    48600 ataccotggtg gcgcttgaag cagagcgtga tggtcaaggc ctgactggga acgctgttct    48660
caattcactg atcactgcgc agctggctgc atttgaaagc ggtgaccaca agaacaccaa    48720
gatgtactcc gatgagatca agaagcttat cacggagggc atcaagacat ctaccgttgc    48780
tgaggcagtc caacgagcaa tcgctgggaa gccttcgctg gtagaagaaa tcctcaccag    48840
gccgttaagc gtcgaccttg acgcgatcac ggttgaggat gcaaaccgag tacgagagat    48900
cttacttgat cccaacaatg ggttcgaaga gttcagtaag tggtgctttg aaatccagat    48960
gggtttcaag tttcagatgc aggattttca ctcgattata tttgagttct gtcagaagat    49020
cgtcaatggc gaaatcgaca gaggcattgt ctgcatccca cctcgtcact cgaagactca    49080
gatactgagt atcttccttc cgctgtactc gttctgcaat aaccccctcca gtcacaatat    49140 aatcacttcg tacgcggacg atgtggtggc ggagtcctcg ggttatatcc ggcagataat    49200
gctggactcg ttgttcatga agatcttccc tgctgtacgt atcgaccaga acaaacgctc    49260
ccttgagcgc tggggtacta cacggtctgg cgtaatgcac gctgtaccaa caggcggtaa    49320
gatgactggt aagggcgctg gctcactgtc accaacctat tcaggatgct tcgtggtcga    49380
cgacgcgatc aaaccgaagg acgcatactc tgcgcctgtt cggaaagaga tcaacgaccg    49440
attcgacaac accttcatgt cgcggcttgc gaacgacggt gaagtccagg acgatgacgg    49500
taatgtcgtc aagtgtccaa gaacacccat ggttatcata atgcagcgag tgcatgatga    49560
cgacctcgtg gggcacatcc ttcgtggtgg ctcctcggat aagtacacat acctgaacat    49620
tccaggtatc gtgacgcctg agtgtggtac cgagaagtgg tacgagaagc tgctgacgaa    49680
gcaagcctac actcacgcgg ttccgtacct ctacgacctg aaacgcggcg aaggtgaatc    49740
tgcgctgtgg ccaagtcgta agagcctcga ttctcttatt gcgatgagaa gcgcgactcc    49800
gtacacattc aactcccagt acatgggtga cccaactgcc agaggcacag gcctgatagt    49860
agaagactgg tggcaggaat ggacggagct tccgttagat gatatcgctc gcgcattcat    49920
gacggcagat acagcctcaa ccaagcagga ctactcagat tactccgtga tctgttattg    49980
gctcctgact aagaaaggca atctgtactt agcggatgtt gagctgggga aatacgagac    50040
accagagttg atgaaagtag tagtcgactt ctggaagaaa cacacgcaat tggatctacg    50100
gtatcctatg ctgctcccga cggcgctgta catggaagat aagtcctctg ggcaattcct    50160
gaaccagcag ttcacgagag acgggcaagt gcgtgttctc ccagttccga agataaatc     50220 ttcgggtgat aagattgctc gattcctaaa cactgtgccg tacttcgcac agggcaggat    50280
ttatttccct gcagaacaca acacaaagc acacataatg cgagaaatcc ttggtatgac     50340
tggggaaggt tctggtacag atcacgacga cgttgtagat aacgtgtctg acgccgtagc    50400
cgtagcattc agtgcccaga ctgctaacta tgcagcctgg atgtaaggag aagctaatgg    50460
gtatcaagac ccgcctggac caacggtctg aaggcaacaa ccgtatgatg ctggtcgatt    50520
ccgccactgg tgaaatcgta gccatcatct ccgcagtgtc caacaaagtc gagatcgaag    50580
tcgagaccgc gaagggcctg cacatcgaga agccgaacgg ttctccagc aaacgctaag     50640
```

```
gacaatcaat gtctgaacct accaatgcac tggcgaagcg tgaggaagac ttccgcgctc   50700
gtctgatgat gcatgacggt ctagagaact tcatgaccgg tctcggcact ggcaaagaca   50760
agaactcgta caacgagtgg atcaggtctg gccggaaccg tgatcatgaa caactcatcg   50820
tcaggtacag ggaagactgg gttgctcaga aagtttgcaa catcctgccg gaagacatga   50880
ctcgggagtg gcgccgatgc agtacacccg aagccatcga ggctgatgat gaattccata   50940
tcagccaact cttccgtgag gcgtacactt gggctagagt gttcggtact gctgctatta   51000
tccttgacct taagggtact ggccgtgcag agacaccgct cgacctgagc cgcctcaagc   51060
cgggatgcat cagaagtctc caggtagttg atcgtacacg gctgatgccg tcaggtacgg   51120
ttgaaatgaa cccgatggat ccggagtacg gctacccgca gcattacatg ctgggcggct   51180
ccacactgca aatccaccgg actcgtattc tgcgctttga agggactccc ctcaccagat   51240
acgagaactg gaagaaccag tggtactcag actcaaccct gatcccgctg tgtgagacca   51300
tcgacaactt ccacacggct gcgcaatccg cgtctgcctt ggttaacgaa gcaaacgtcg   51360
atgtggtcac tgtccaaggg ctgcagaatc tgttgaccaa ccctgctggc gaggctgctt   51420
tgtataagcg cttccgcatg atgaagcaga tgaagtccaa ccacaacatt ctgctgctgg   51480
acaacaccga agagtacagc cccaagacca tcgcactgaa tggcgtcaag gatctcatct   51540
gggaatactt acgtatcatt gctgctgctt gtggtgtacc tgcaacgaga ttcctctcgg   51600
cgtcgcccga tggcatgaac gcaactggcg agtcagacct caataactat attgacctgc   51660
tgcgccagaa acagaagtct gtctttgaca aacgactgcg tgtcatcgat aagattctcg   51720
ctgctcactt cggcatccag ccgttcaagt atacctggaa ctgcgcattc ccagagtcgt   51780
ccctgcagaa ggaagaacgc cggaacaaac tggccgattc attgcagaag cttgtagttg   51840
gtggcgtcat tactggcgat actgctatca agattatgga agaagagcat actttcggag   51900
acattgatct cgggaaggca ccgccacctc ctcctaaacc gtcaaatggg gaaaactcca   51960
aatgatcaaa atgtctcaac ggatcacgtt ccgagacgaa gctgagcttg agctgacccg   52020
ctttgttgat gaaggctgtg accttccaac tcagcgcaag ttcaaggata gcggtgcgat   52080
gattgctccg gcgaccattg cccgcaccgg catcatgaac tactctgctg gccactgcgg   52140
caagttgttc tccgactggc ctgcgaccaa gatcgtgcga gtgatgactc gtgccgaaga   52200
cctgttccac gccgactccc tcgaactgta ccgttctgcc ccgatcacta tcggccaccc   52260
tgacgaagac gtgtccatcg acaacgccgg ctggctgcag aagggtaacc tcgatggtat   52320
tcctttccag gatggtgagc agctcgccgg tcacgtagtg ctgacccaca aggaagctct   52380
ggacctggtg gatgctggtg taagccaact gtcctccggt cacgacgcta ccctgatccg   52440
cctgtctgac gaagatgctg cgcgactggg ctacgacgcc tacaagacca acatccgtcc   52500
gaaccacgta gccatcgttc gaaaggccg tgccggctct gcccgcatcg ctgacgaaga   52560
cgaaggcgct ggcaagacca aggaagacga aggtcaggtc aagatgtacg accaggccca   52620
cgtgtccggt ctggaagctc agctggaagc atctgtcact ctggcagacg gcctgaaagc   52680
cgaggtgcaa gagctcaagc tcaagatcac cgacgaagcc atccaggtgt tggtcaacaa   52740
gcgtctggag ttcatgaccg aggtggctca gtttactgat gctgatatct ccggcatgtc   52800
cgagctggat gcgaagaaga ttgctatcaa ggatgcctgt ggtaaagact acagcgaccg   52860
tgacgagcac ttcatcaacg cccgctcagg cattctcctg gaagaaggca ccgaatccgg   52920
tggcaccgat atctcccagg ccttccgtga tcacattaag gatccggaaa tcaaagcgaa   52980
```

```
gtccgagcct acgcagagcg aatccgcccg ccagcgtatg atcgaccgtc aatccaagta    53040
atcgaggaca caacatgccc gttcaagaat atcacatcaa tacccgtgac gaagtcgaag    53100
gtcaactcta cggcctgcaa cagactcgtg ccgacatcca gactggtttt gccgaagatg    53160
tcagcggcat cccgttcggt aaggccgtta aagtcggtgc tggcccgcgt ggcttcctgc    53220
tgggtgccgc tggcgctcac gtagacggca tcgtcctgcg tcagatcgac cgtgaagctg    53280
ccaagcgccc gtccgacggc accgtagtct tccgcaaggg cgactccctg ccggtgtgct    53340
ccgatggccg tgtggtcgtc aaggtgatgg acgctggtgc catcgttcgt ggtcagaagg    53400
tattcgtgca tcaagccaac ggtaccttcc acgtagctac tggtgctggc ctggtcgaag    53460
cctccaacgt tgtttggggc atcggtaaga ccgccgctgt cggcgacctg gtccacgttg    53520
taatcaccaa cgctgacgta gcctaattgg ctgagccgga gcaatccggc tcttctccct    53580
cgattcaagg aatacaaatg tcccgtaaag taaagttctt cgacgcagag caaggcaaag    53640
aagtagagat cgaactgcgt gctgatatcg ctcgcctgat cgaccaagat gttcgtctga    53700
ccgatgacga cggcatcttc ttccagcgtc aactggaagc cattgaagct cagacctacg    53760
atgtgctcta tccggacctg gaagctcgta gctgcttcaa aaccaacacc ttcggtggtg    53820
ctggcgcccg taccctgacc taccgttctt tcgaccgtat cggtaaggcc caggtcatca    53880
acgctcgcgc taccgacctg ccgaagtccg acatctccgg taaagaatac tccatcactg    53940
tcaagtccgt aggcgtcgct tacgactacg acatcgacga gatcgctgcc gccaagatgg    54000
ctggtatgcc gctggaagct cgtaagacca tggctgctcg ccgtggctac gaggagtaca    54060
tcaactccgt tgtatggcgt ggtgatgctg atgccggtct gggtggcctg ttcaccaaca    54120
ccgacatccg ccgtaccgct gttgcccaag gcactgctgg taccaccggc tggagcacca    54180
agactccgga cgaagtgatc gctgacctga cccacgcttg tggcgacatg tacgcgacca    54240
ccaagaagat ccatgctccg aaagagatct ggatgtcgac cctgaactgg aattacctgt    54300
tctccactcc gcgtagcccg atgtctgaca agaccatcgg tgactacttc tgcgagaaca    54360
accagttcgg catcaagaag gagaacatca agccgctgaa cgagctggct gaaggtatcc    54420
ccatgggcac cggcgcaggc tctcactgtt t    54451
```